US011430565B2

(12) United States Patent
Vadali et al.

(10) Patent No.: US 11,430,565 B2
(45) Date of Patent: Aug. 30, 2022

(54) INVENTORY TRACKING SYSTEM WITH AVAILABILITY IDENTIFICATION

(71) Applicant: Medtronic, Inc., Minneapolis, MN (US)

(72) Inventors: KVS Manoj Kumar Vadali, Hyderabad (IN); Venkata Prasad Mooram, Hyderabad (IN); Nissy Bandaru, Hyderabad (IN)

(73) Assignee: MEDTRONIC, INC., Minneapolis, MN (US)

( * ) Notice: Subject to any disclaimer, the term of this patent is extended or adjusted under 35 U.S.C. 154(b) by 245 days.

(21) Appl. No.: 16/814,015

(22) Filed: Mar. 10, 2020

(65) Prior Publication Data
US 2021/0287782 A1    Sep. 16, 2021

(51) Int. Cl.
| | |
|---|---|
| *G16H 40/20* | (2018.01) |
| *G16H 40/67* | (2018.01) |
| *G16H 40/40* | (2018.01) |
| *G06T 7/00* | (2017.01) |
| *G06Q 10/08* | (2012.01) |

(Continued)

(52) U.S. Cl.
CPC ....... *G16H 40/20* (2018.01); *G06Q 10/06312* (2013.01); *G06Q 10/087* (2013.01);
(Continued)

(58) Field of Classification Search
CPC ........ G16H 40/20; G16H 40/40; G16H 40/67; G06Q 10/06312; G06Q 10/087;
(Continued)

(56) References Cited

U.S. PATENT DOCUMENTS

| | | |
|---|---|---|
| 9,204,823 B2 | 12/2015 | Derenne et al. |
| 9,664,510 B2 | 5/2017 | Nathan et al. |

(Continued)

FOREIGN PATENT DOCUMENTS

WO    WO-2011020505 A1 *   2/2011    ............. A61B 34/20

OTHER PUBLICATIONS

Darwish et al. "The impact of the hybrid platform of internet of things and cloud computing on healthcare systems: opportunities, challenges, and open problems." Journal of Ambient Intelligence and Humanized Computing, vol. 10, pp. 4151-4166 (2019) (Year: 2019).*

(Continued)

*Primary Examiner* — Linh Giang Le
(74) *Attorney, Agent, or Firm* — Fox Rothschild LLP

(57) ABSTRACT

A system comprising a plurality of imaging devices, each imaging device being associated with a known location and memory having programming instructions stored thereon. The system comprises one or more processors having programming instructions which when executed to cause the one or more processors to receive images from at least one imaging device, recognize in the received images of the at least one imaging device at least one portable machine, determine a location the portable machine based in part on the location of the at least one imaging device; and predict current availability of the at least one portable machine based on the received images, detected features of the recognized at least one portable machine, and at least one object in a scene of the received image.

20 Claims, 16 Drawing Sheets

(51) Int. Cl.
*G06T 7/73* (2017.01)
*G06Q 10/06* (2012.01)

(52) U.S. Cl.
CPC .............. *G06T 7/73* (2017.01); *G06T 7/97* (2017.01); *G16H 40/40* (2018.01); *G16H 40/67* (2018.01)

(58) Field of Classification Search
CPC ... G06T 7/73; G06T 7/97; G06T 2207/10016; G06T 7/75
See application file for complete search history.

(56) References Cited

U.S. PATENT DOCUMENTS

| | | |
|---|---|---|
| 10,157,536 B2 | 12/2018 | Zuckerman et al. |
| 2013/0124227 A1 | 5/2013 | Ellis |
| 2019/0000382 A1 | 1/2019 | Fitzpatrick |
| 2019/0046126 A1 | 2/2019 | Owen et al. |
| 2019/0198161 A1 | 6/2019 | Lee et al. |
| 2019/0326015 A1 | 10/2019 | Cannell et al. |
| 2019/0371458 A1* | 12/2019 | Gonzalez .............. G16H 40/20 |
| 2019/0378074 A1 | 12/2019 | McPhatter et al. |

OTHER PUBLICATIONS

Real-time location system-based asset tracking in the healthcare field: lessons learned from a feasibility study, Sooyoung Yoo, et al. BMC Medical Informatics and Decision Making, (2018) 18:80 https://doi.org/10.1186/s12911-018-0656-0.
Asset Management, Enterprise Location Services™, CenTrak® Jul. 30, 2018.

* cited by examiner

INVENTORY TRACKING SYSTEM WITH AVAILABILITY IDENTIFICATION

TECHNICAL FIELD

The present disclosure generally relates to an inventory tracking system for locating inventory and determining availability of the inventory.

BACKGROUND

Around 45% of hospitals believe they do not manage their medical assets properly. In addition, the average hospital worker spends an average of 72 minutes searching for assets during each shift. Time is of the essence in hospitals, and not being able to track down a missing asset can be detrimental for the patient. It is estimated that over $1 million of wages are lost per year for the time staff spends on searching for assets. According to the Northern Illinois Hospital, $4,000 are lost per day looking for assets.

It is estimated that more than 50% of the operating costs of a hospital are related to labor. With clinical hours wasted on searching for portable machines needed to deliver healthcare therapies or diagnostic testing, for example, both scheduling the use of the portable machines and human resource availability can be impacted.

RFID (Radio Frequency Identification), and BLE (Bluetooth Low Energy) based asset tracking systems are current solutions in place to address the hospital asset tracking, especially for portable assets. However, there are challenges associated with the existing solutions for wide-scale adoption. Installation of existing solutions are specific to each hospital, as each floor can have a different floor plan, for example. Installing these solutions requires a significant investment in money and time. Moreover, such solutions require repeated expenditure as assets are added and removed from service. Every new item addition to the fleet needs a new sensor. Accordingly, the hospital may need to contact the solution providers to program and add the new device to the tracking system.

Continuous exposure to radiation can cause serious health issues for both caregivers and patients in hospitals due to RFID/BLE communications. Moreover, existing asset tracking systems do not provide any information about the availability of the equipment (in-use or not in-use).

SUMMARY

In an embodiment, an inventory tracking system is provided for locating inventory and determining availability of the inventory for display on a graphical user interface (GUI).

An aspect of the invention includes a system comprising a plurality of imaging devices, each imaging device being associated with a known location and memory having programming instructions stored thereon. The system comprises one or more processors having programming instructions which when executed to cause the one or more processors to receive images from at least one imaging device, recognize in the received images of the at least one imaging device at least one portable machine, determine a location the portable machine based in part on the location of the at least one imaging device; and predict current availability of the at least one portable machine based on the received images, detected features of the recognized at least one portable machine, and at least one object in a scene of the received image.

Another aspect of the invention includes a computer-implemented method comprising, by one or more processors, receiving images from at least one imaging device having a known location; recognizing in the received images of the at least one imaging device at least one portable machine; determining a location the portable machine based in part on the known location of the at least one imaging device; and predicting availability of the at least one portable machine based on the received images, detected features of the recognized at least one portable machine, and at least one object in a scene of the received image.

A further aspect of the invention includes a tangible and non-transitory computer readable medium having programming instructions stored thereon which when executed to cause the one or more processors to: receive images from at least one imaging device from a known location; recognize in the received images of the at least one imaging device at least one portable machine; determine a location the portable machine based in part on the known location of the at least one imaging device; and predict availability of the at least one portable machine based on the received images, detected features of the recognized at least one portable machine, and at least one object in a scene of the received image.

DETAILED DESCRIPTION

Figure 1:
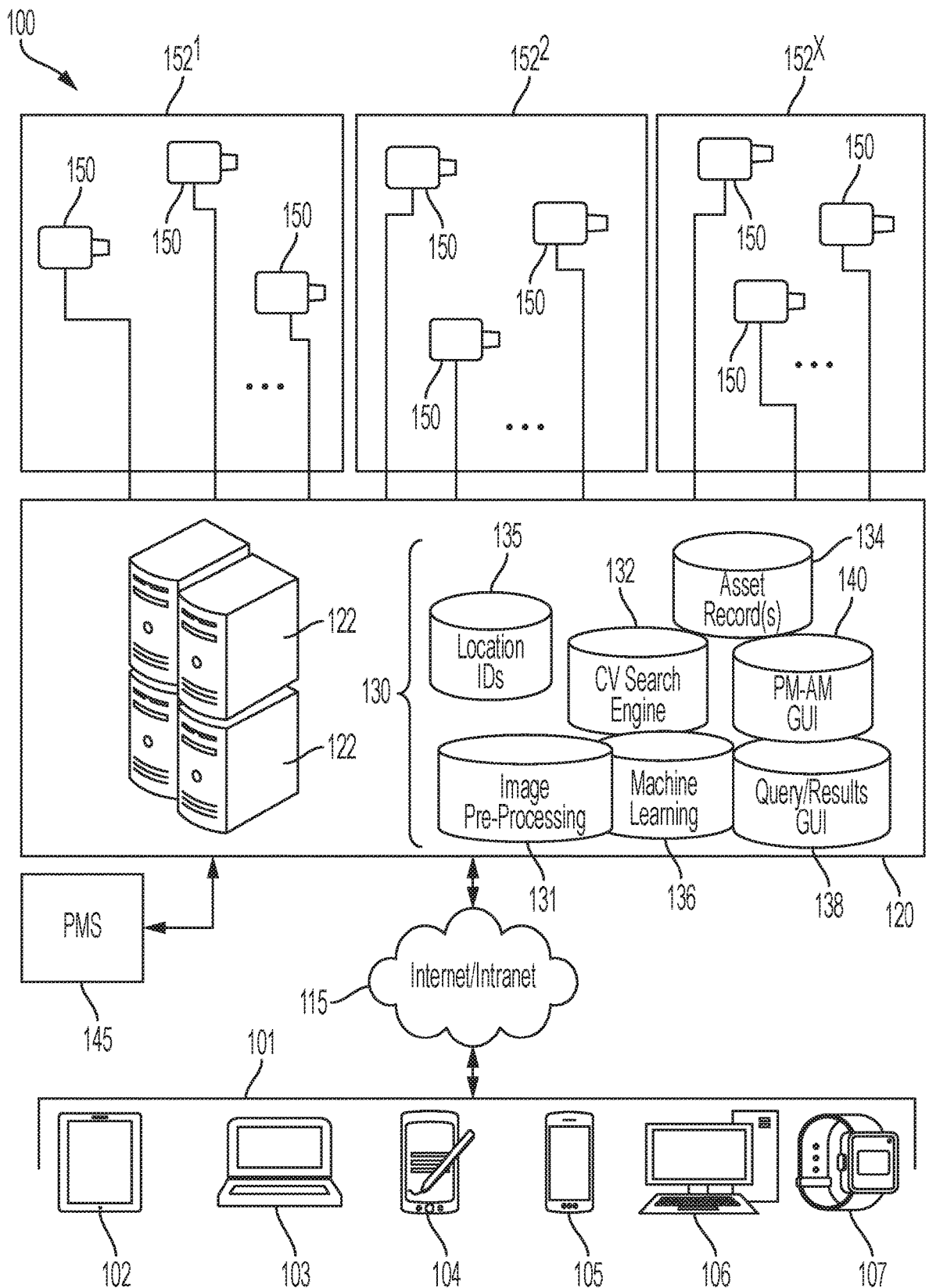
FIG. 1 illustrates an example inventory tracking system with availability identification.

The present invention may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting.

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other. Generally, similar spatial references of different aspects or components indicate similar spatial orientation and/or positioning, i.e., that each "first end" is situated on or directed towards the same end of the device. Further, the use of various spatial terminology herein should not be interpreted to limit the various location techniques or orientations for identifying objects or machines.

An "electronic device" or a "computing device" refers to a device or system that includes or shares a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions. Examples of electronic devices include personal computers, servers, mainframes, virtual machines, containers, cameras, tablet computers, laptop computers, media players and the like. Electronic devices also may include appliances and other devices that can communicate in an Internet-of-things arrangement. In a client-server arrangement, the client device and the server are electronic devices, in which the server contains instructions and/or data that the client device accesses via one or more communications links in one or more communications networks. In a virtual machine arrangement, a server may be an electronic device, and each virtual machine or container also may be considered an electronic device. In the discussion above, a client device, server device, virtual machine or container may be referred to simply as a "device" for brevity. Additional elements that may be included in electronic devices are discussed in the context of FIG. 1.

The terms "processor" and "processing device" refer to a hardware component of an electronic device that is configured to execute programming instructions. Except where specifically stated otherwise, the singular terms "processor" and "processing device" are intended to include both single-processing device embodiments and embodiments in which multiple processing devices together or collectively perform a process.

The terms "memory," "memory device," "data store," "data storage facility" and the like each refer to a tangible and non-transitory device on which computer-readable data, programming instructions or both are stored. Except where specifically stated otherwise, the terms "memory," "memory device," "data store," "data storage facility" and the like are intended to include single device embodiments, embodiments in which multiple memory devices together or collectively store a set of data or instructions, as well as individual sectors within such devices.

In this document, the terms "communication link" and "communication path" mean a wired or wireless path via which a first device sends communication signals to and/or receives communication signals from one or more other devices. Devices are "communicatively connected" if the devices are able to send and/or receive data via a communication link. "Electronic communication" refers to the transmission of data via one or more signals between two or more electronic devices, whether through a wired or wireless network, and whether directly or indirectly via one or more intermediary devices.

In this document, the term "imaging device" refers generally to a hardware sensor that is configured to acquire images, such as digital images. An imaging device may capture still and/or video images, and optionally may be used for other imagery-related applications. For example, an imaging device can be a video camera or a still image camera. The imaging device may be part of an image capturing system that includes other hardware components. For example, an imaging device can be mounted on an accessory such as a monopod or tripod. The imaging device can also be mounted to a wall or ceiling. The imaging device may be body worn, head mounted, hand-held or affixed to stationary or mobile electronic devices. The imaging device may include a transceiver that can send captured digital images to, and receive commands from, other components of the system.

Other terms that are relevant to this disclosure are defined at the end of this Detailed Description section.

The following discussion includes a description of the inventory tracking system with availability identification and/or utilization data/metrics capturing and reporting.

FIG. 1 illustrates an example inventory tracking system 100 with availability identification according to an embodiment. As illustrated in FIG. 1, the system 100 may comprise a vision computer system 120. The computer vision system 120 may comprise memory 130 having programming instructions stored thereon. The computer vision system 120 may comprise one or more servers or computing devices 122 configured to execute the programming instructions stored in memory 130. The server or computing device 122 will be described in more detail in relation to FIG. 10.

In an embodiment, the computer vision system 120 may interface with a patient monitoring system (PMS) 145. A VitalSync platform by Medtronic Inc. provides patient monitoring data to the PMS 145 during medical procedures or therapies. Nonetheless, other patient monitoring systems may be used. The system 100 can integrate asset monitoring along with the patient monitoring activities to provide a complete integrated solution for hospitals using a dual-use graphical user interface (GUI).

The memory 130 may include a plurality of memory devices and/or databases. The memory 130 may include programming instructions 132 for conducting a computer vision (CV) search of an asset. The programming instructions 132 will sometimes be referred to as the "CV search engine 132." The memory 130 may include programming instructions 131 for pre-processing a video stream into one or more still images for input into a CV search engine 132. The memory 130 may include asset record(s) 134 for each registered asset to be tracked, located and availability predicted. The asset record 134 will be described in more detail in relation to FIG. 5.

The memory 130 may include programming instructions 135 associated with location identifier (ID) data, such as, location landmarks, landmark features, imaging device locations, virtual boundaries, and information associated with the facility layout and floor plans. This information may be used to identify a location of an asset and generate location data based on one or more of the location ID data.

The CV search engine 132 may be a data analytics engine based on supervised learning algorithms, which takes labeled images and known statistical (manufacturer) data as input and extracts the features to build/train a predictive model of the machine learning algorithms 136 for a particular asset. The machine learning algorithms may use both supervised and unsupervised algorithms.

The memory 130 may include programming instructions representative of machine learning algorithms 136 to track, locate and predict availability of an asset using the predictive mode and classifier. The machine learning algorithms 136 may include one or more predictive models. The machine learning algorithms 136 may include a predictive model for each asset or asset type. A predictive model may be required for location identification within the facility or hospital using data analytics associated with the location ID data, captured location data and/or imaging device location data. A predictive model may be used for one or more virtual boundaries. A predictive model may be used for real-time availability identification.

Common algorithms for performing classification processes by the machine learning algorithms may include a support vector machine (SVM), boosted and bagged decision trees, k-nearest neighbor, Naïve Bayes, discriminant analysis, logistic regression, and neural networks.

A predictive model with help of available knowledge (asset record) and identified features from the images may identify the asset and usage or availability conditions. The predictive model may be used for maintenance scheduling. For example, if an asset is needed for maintenance, the asset can be readily taken out of the field with less idle time of the asset.

The memory 130 may include programming instructions for generating and displaying a query and results graphical user interface (GUI) 138 on a user electronic device 101. The query and results GUI 138 will be described in more detail in relation to FIGS. 2A and 2B. The query and results GUI 138 being configured to allow a user to initiate a search for a location of a selected one asset and provide the results of the query.

The user electronic device 101 may, for example, include a tablet 102, a laptop 103, a personal digital assistant (PDA) 104, a smart phone 105, a personal computer 106 and a smart watch 107. The user electronic device 101 may include other electronic devices with display devices which may be head mounted or body worn. A head mounted display (HMD) device may be integrated into glasses or googles. The user electronic device 101 may include a global positioning system and/or inertial navigation system for estimating a geographical location of the user electronic device 101, such estimation of geographical location being well known in the art. The inertial navigation system may include accelerometers, magnetometer and/or gyroscopes. The inertial navigation system may include an in inertial measurement unit (IMU).

The user electronic device 101 may access the query/results GUI 138 of the computer vision system 120 via a communication network 115 such as an intranet or the Internet. The electronic device 101 may communicate over the communication network 115 using Internet standards or Ethernet standards. The network communications may use wired or wireless communication media and related protocols associated with the platform type of the electronic device.

The memory 130 may include programming instructions for selectively generating and displaying asset monitoring (AM) data generated by the computer vision system 120 for display by an integrated patient monitoring (PM) and asset monitoring (AM) GUI 140. The PM-AM GUI 140 being configured to selectively display patent monitoring data from the PMS 145. The PM-AM GUI 140 will be described in more detail in relation to FIGS. 3A-3B.

The system 100 may comprise a plurality of imaging devices 150. The plurality of imaging devices 150 are shown, for example, in groups of imaging devices $152^1$, $152^2$, ..., $152^X$, each group of imaging devices $152^1$, $152^2$, ..., $152^X$ being associated with a subset of locations within a space. Each imaging device 150 may be associated with a plurality of locations. One or more the groups imaging devices $152^1$, $152^2$, ..., $152^X$ may be pre-existing imaging devices being piggybacked on by the system 100. For example, the solution may use existing imaging devices in a facility that is used for security. The solution may use existing imaging devices in designated areas such as a procedure room, an emergency room and other areas. The solution may use cameras that are on existing stationary electronic devices with its location identifier, such as floor number, wing number, etc., being communicated to the computer vision system 120.

The plurality of imaging devices 150 may be stationary and a part of a closed circuit television (CCTV) system to capture video or images within a field of view (FOV). In another example, one or more of the groups of imaging devices $152^1$, $152^2$, ..., $152^X$ may include mobile cameras. The plurality of imaging devices 150 may include a combination of stationary and mobile imaging devices.

The system 100 may utilize the CCTV real-time video footage to identify and track the hospital assets. Many of the hospitals are equipped with closed circuit (CC) cameras for security purposes. The system 100 may piggyback on the existing CCTV system where available to generate real-time captured images. The images of the CCTV footage can be utilized by machine learning software algorithms the computer vision system 120 to identify, locate and determine availability of a hospital asset. This solution does not require any RFID or BLE sensors to be placed on or integrated into the asset or in the facility for the purpose of location tracking and availability identification.

Figure 5:
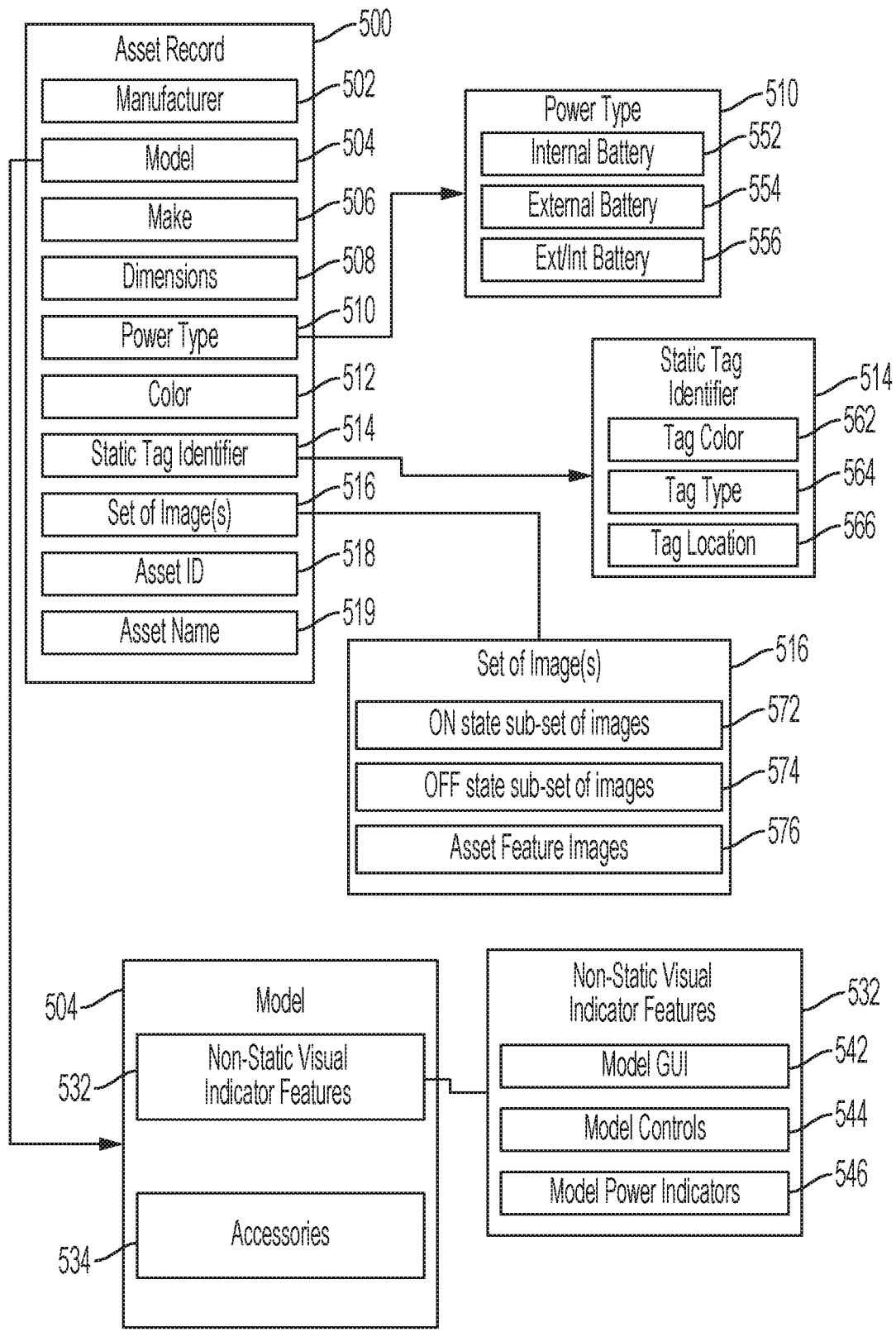
FIG. 5 illustrates an example asset record.

An asset may be added to the system 100 by adding an asset record, as described in more detail in relation to FIG. 5, with a set of images of the new asset. In case of identical equipment (e.g., more than one portable x-ray machine of same make and model), a static visual (tag) identifier may be placed on each asset body of the machines of the same make and model to identify the assets separately. For example, colored tags, flags or ribbons, which are visible up to $360$ degrees, may be affixed to the asset body to differentiate these otherwise identical assets visually.

Figure 2A:
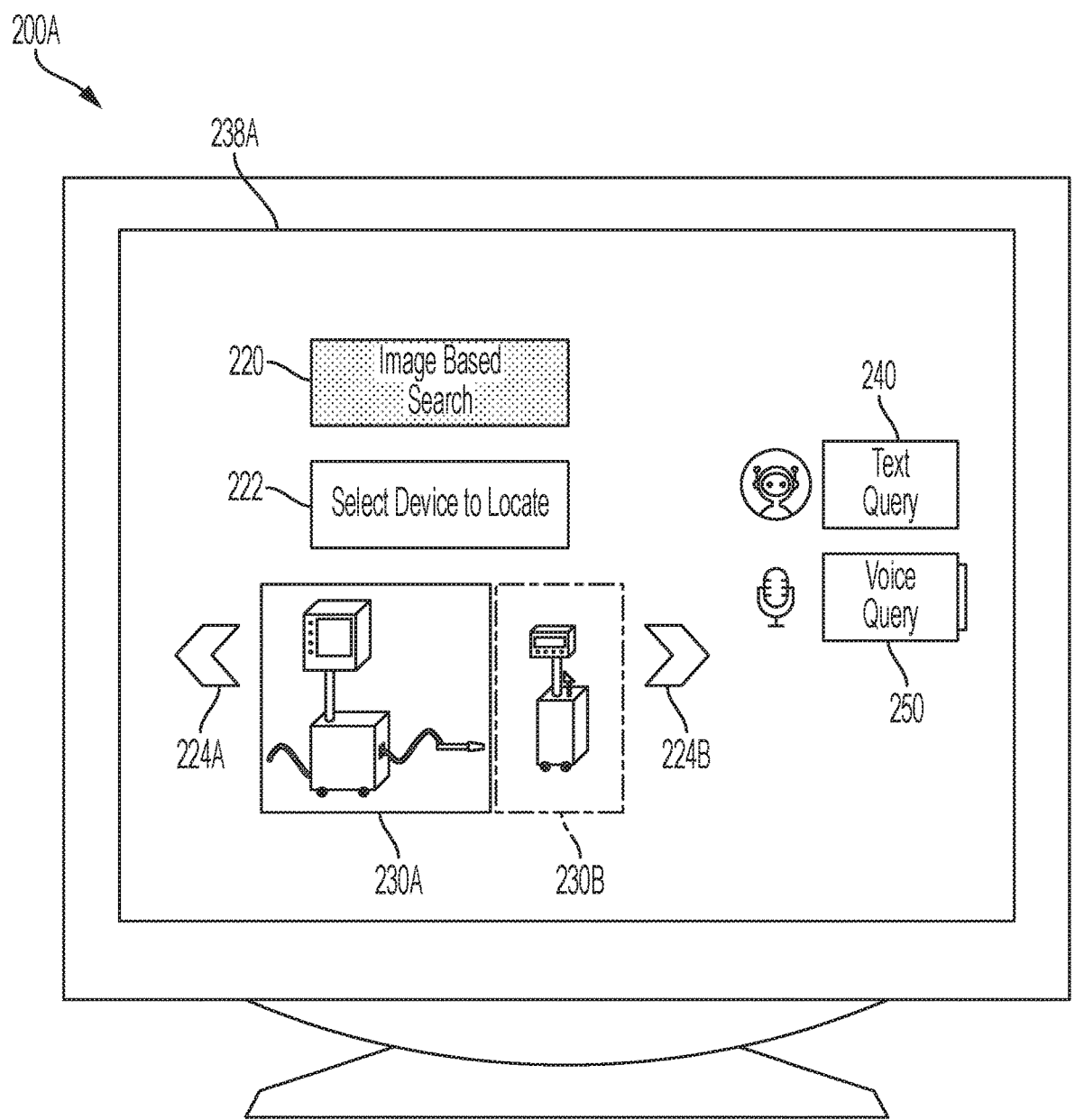
FIG. 2A illustrates an example query graphical user interface (GUI) for selecting and querying a location and real-time availability of an asset, the GUI displayed on a display device.

FIG. 2A illustrates an example query graphical user interface (GUI) 238A for selecting and querying a location and real-time availability of an asset. The GUI is shown displayed on a display device 200A. The query GUI 238A may include a plurality of query-mode selector tabs 220, 240 and 250. The selector tab 220 provides for an image-based search or query. In the example, the selector tab 220 for an image-based search is selected, as denoted by the dotted hatching. The query GUI 238A allows the user to select an image-based search using a selected image.

The query GUI 238A may retrieve and display a plurality of searchable asset images 230A and 230B with at least one being selectable for location and availability identification. While, two asset images are depicted in the example, in some embodiments, one or more asset images may be displayed.

The query GUI 238A may include navigation buttons 224A and 224B to allow a user to scroll through images of a plurality of assets with asset records 134 stored in memory 130. The navigation button 224A is depicted as an arrow pointing in the left direction. The navigation button 224B is depicted as an arrow pointing in the right direction. Nevertheless, other navigation button types, slide bars, or navigation tools may be used.

The query GUI 238A may include a prompt display field 222 for the user to select a particular asset from the asset images 230A and 230B shown. Assume for the purposes of discussion, that asset image 230B was selected, denoted by a long dash, short dash box.

The selector tabs 240 and 250 may allow for a text query and a voice query, respectively, for selecting an asset to be located and availability identified. The query GUI 238A may be voice responsive to generate a query using the selector tab 240. The user may provide a voice input which is received by the query GUI 238A interpreted for at least one voice command of selection of a particular asset. The voice command may speak the name or identifier of an asset identified in the asset's record. The voice command may cause the GUI 238A to display a list of assets of a particular type, such as ultrasound machines, X-ray machines, etc. The voice input may cause the GUI to display the ultrasound machines of the tracked fleet, by way of non-limiting example. The use may then select, with a voice command or other machine-to-user interface input, an asset to which to track, locate and determine availability.

Machine-to-user interface may include a microphone, a mouse, keypad device, touch-sensitive screen of a display device.

The selector tab 250 may allow a text-based query to be input through the GUI 238A. The user may enter text using a keypad device or a touch-sensitive screen. The text may include a string of alphanumeric characters representative of an asset for which to query its location and determine availability.

Figure 2B:
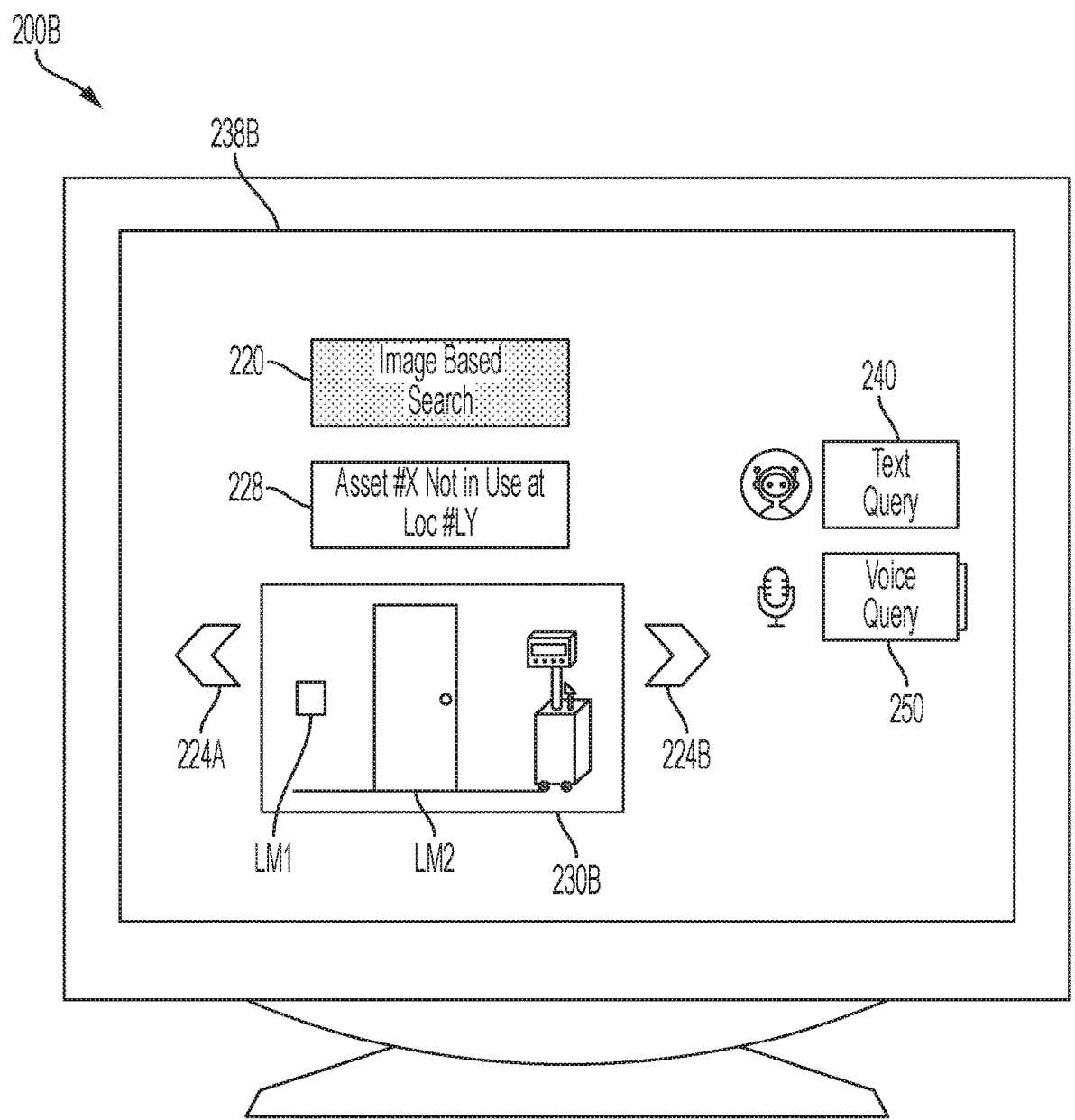
FIG. 2B illustrates an example results graphical user interface (GUI) displaying a location of the asset with real-time availability identification.

FIG. 2B illustrates an example results graphical user interface (GUI) 238B displaying a location of the asset with real-time availability identification on a display device 200B. The results GUI 238B may be similar to the query GUI 238A. However, the results GUI 238B may display availability of an asset such as in results data field 228. The results data field 228 may include an asset identifier "#X" wherein the reference indicator "#X" may include numeric or alphanumeric characters. The results data field 228 may include an asset location identifier "#LY" wherein reference indicator "#LY" may include numeric or alphanumeric characters.

In FIG. 2B, the image 230B displayed by the results GUI 238B may include a real-time captured image of the asset being queried. The image 230B may include captured landmarks LM1 and LM2, by way of non-limiting example. By way of non-limiting example, landmark LM1 may be a plaque on the wall. Landmark LM2 may be a door to a patient's room. Other landmarks will become evident based on the description herein. However, describing each and every possible landmark is prohibitive.

The results GUI 238B is illustrated displaying an image of a single asset that is available. However, the results GUI 238B may display all assets of a particular type including the real-time availability of the fleet of assets by type being queried, for example. The navigation buttons 224A and 224B may allow a user to scroll through images of a plurality of assets of the type queried which have been located and availability identified. For example, the results may include an asset that is available and which is in closer proximity to the current user's location. The user may scroll through the results via the GUI 238B to find the best available asset. In an example, the vision computer system 120 may use a current geotagging location information of the electronic device 101 to organize the list of available assets of a fleet displayed by the GUI 238B. For example, some facilities may have multiple buildings. The vision computer system 120 may list or rank the available assets in an order based on the building in which both the asset and the electronic device 101 are currently located. The vision computer system 120 may list or rank the available assets in an order based on an estimated distance between the asset and the electronic device 101.

Results information provided in the GUI 238B may include an asset location (example: PB980 ventilator is in $2^{nd}$ Floor ICU). Results information provided in the GUI 238B may include real-time asset availability using the words, such as "in use," "not in use," "available to use," "available," "unavailable," "occupied," "unoccupied" or variations thereof, by way of non-limiting example. An example statement may include "General Electric Portable x-ray machine is available to use @$5^{th}$ floor Operation Theater." The term "General Electric" identifies a manufacturer. The "Operation Theater" may identify a zone on the $5^{th}$ floor. The term "x-ray machine" may identify an asset type.

Figures 3A, 3B:
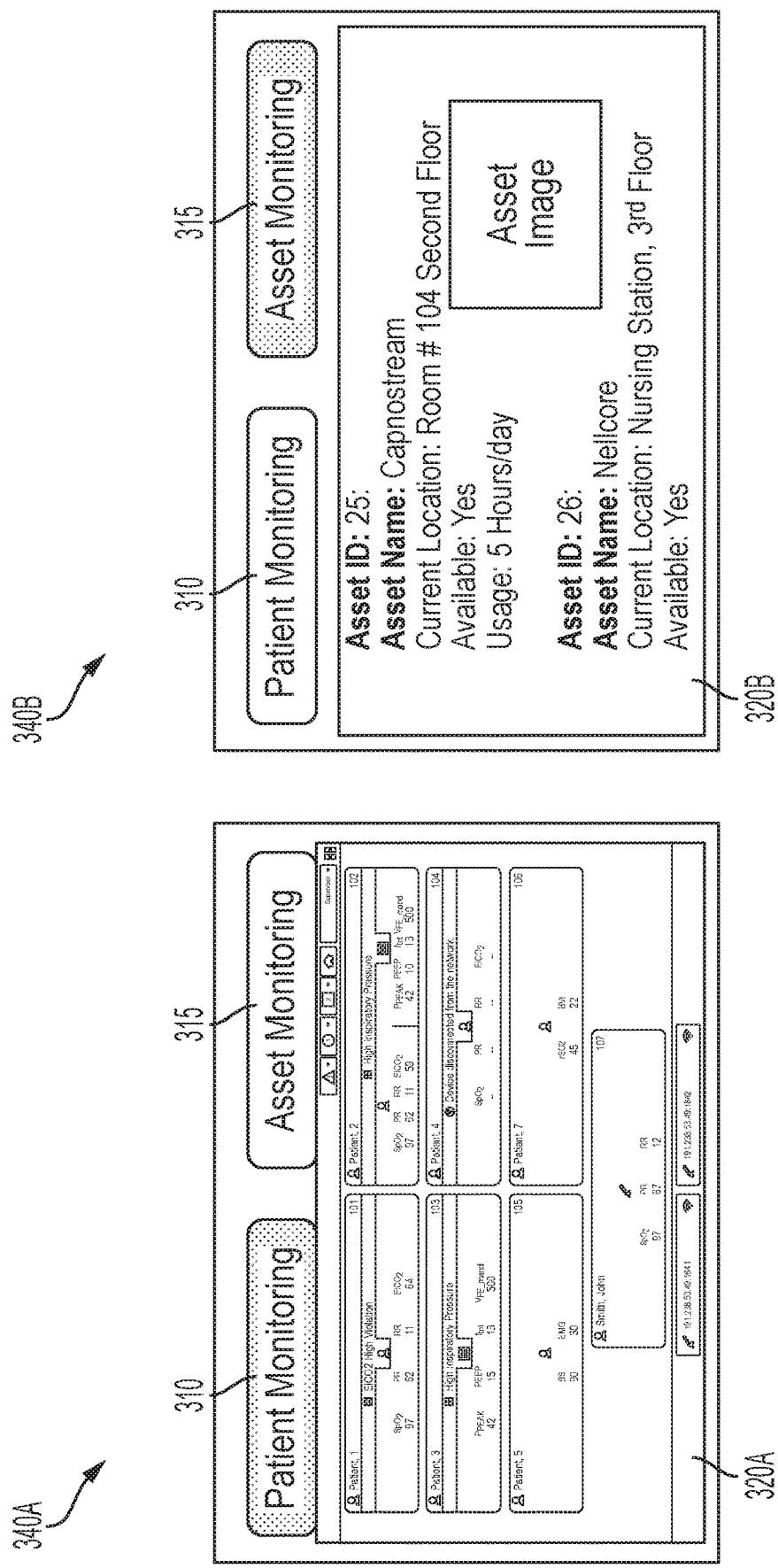
FIG. 3A illustrates an example patient and asset monitoring GUI with patient monitoring data displayed.
FIG. 3B illustrates an example patient and asset monitoring GUI with asset monitoring data displayed.

FIG. 3A illustrates an example patient and asset monitoring GUI 340A with patient monitoring data displayed. The patient and asset monitoring GUI 340A includes a patient monitoring tab 310 and an asset monitoring tab 315. In FIG. 3A, the patient monitoring tab 310 is selected, as denoted by the dotted hatching of the patient monitoring tab 310. Patient monitoring data generated by certain assets is collected by the PMS 145, as will be discussed in more detail in relation to FIG. 4B. The sensors (not shown) of the asset captures patient health vitals or parameters and may send the captured patient data to the PMS 145 and/or asset computing system. For example, the asset may include its own computing device with communication units for communicating using wireless or wired communications in the facility. The asset or another user electronic device may be configured to display the captured patient monitoring data or vital statistics or parameter in a display screen 320A. The display screen may be part of a model graphical user interface (GUI), as will be described in FIG. 5. The asset may be used in the performance of a medical procedure. Various health parameter may be collected by sensors of the asset as the procedure is conducted.

FIG. 3A illustrates an example patient and asset monitoring GUI 340B with asset monitoring data displayed. The patient and asset monitoring GUI 340B may allow a user electronic device 101 or other display device to see available assets by selecting the asset monitoring tab 315. Display screen 320B illustrates fields of asset location data and real-time availability status along with an asset identifier.

In the example, the GUI 340B displays one or more of an asset ID, an asset name, a current location, availability and usage. The usage data may be useful to a user if the asset requires recharging of batteries for continued operation.

Figures 4A, 4B:
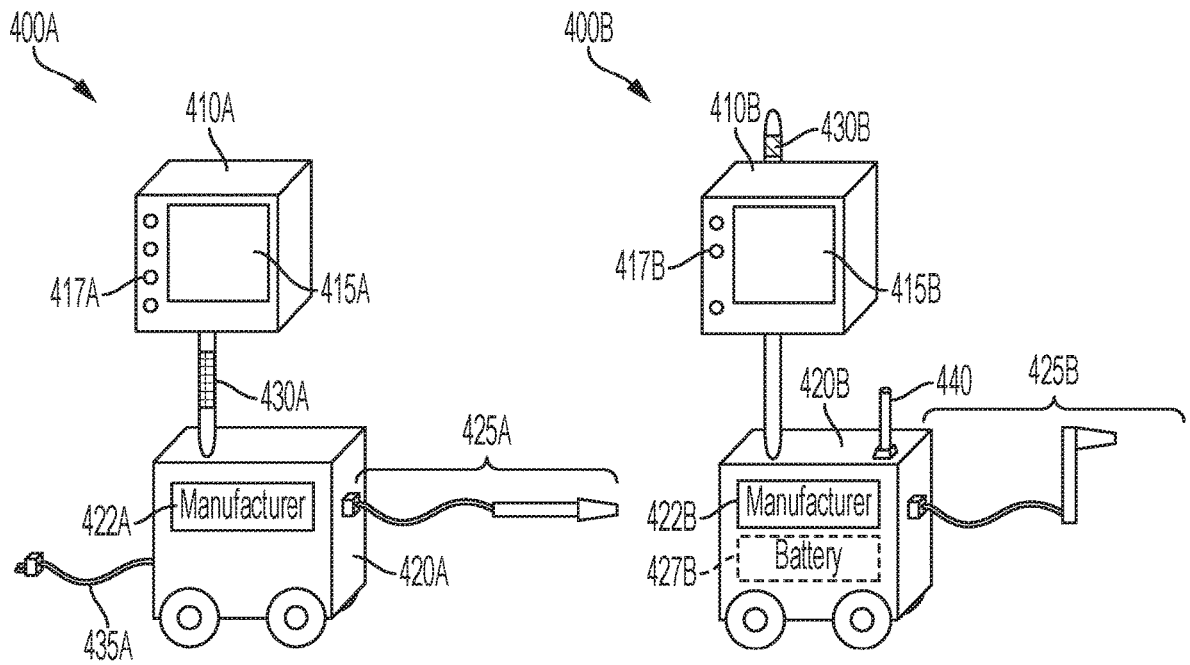
FIG. 4A illustrates an example of a first asset.
FIG. 4B illustrates an example of a second asset.

FIG. 4A illustrates an example of a first asset 400A. The first asset 400A may include an asset body 420A. The asset body 420A may include wheels and a power cord 435A. The first asset 400A may include a first static identifier field 422A and a second static identifier field 430A, the second static identifier field being denoted as square hatching. The first asset 400A may include a monitor device 410A having a display screen 415A. The first asset 400A may include controls 417A, the controls may include one or more of touch sensitive buttons, knobs and switches, for example.

The display screen 415A may provide a non-static identifier for the CV search engine 132. In some example, the controls 417A may provide a non-static identifier for the CV search engine 132. The non-static identifier(s) may be used to determine the current operational state of the asset 400A, as will be described in more detail in relation to FIG. 7A.

The CV search engine 132 may recognize one or more static identifier fields and one or more non-static identifier fields. By way of non-limiting example, a facility may have multiple models of the same asset from the same manufacturer or different manufactures. Thus, the first static identifier field 422A and a second static identifier field 430A may be used to visually identify an asset manufacture and an asset identifier.

In some embodiments, the asset body 420A may be distinguishable by one or more of other static identifiers such as a body color, a body shape, a body size, and a body surface texture, configured to be extracted from an image.

The first asset 400A may include a sensor, probe, and/or treatment applicator 425A configured to be coupled to the asset body 420A. In some embodiments, the sensor, probe, and/or treatment applicator 425A may be removably attached. In other embodiments, the sensor, probe, and/or treatment applicator 425A may be permanently attached. Nonetheless, a sensor, probe, and/or treatment applicator 425A may be identified and extracted to determine a type of asset and/or availability of the asset.

FIG. 4B illustrates an example of a second asset 400B. The second asset 400B may include an asset body 420B. The asset body 420B may include wheels. The asset body 420B does not include a power cord 425B but may include a battery 427B which is not visible externally, as denoted by the dashed box on the asset body 420B. The second asset 400B may include a first static identifier field 422B and a second static identifier field 430B, the second static identifier field being denoted as diagonal line hatching. The second asset 400B may include a monitor device 410B having a display screen 415B. The second asset 400B may include controls 417B, the controls may include one or more of touch sensitive buttons, knobs and switches, for example.

The display screen 415B may provide a non-static identifier for the CV search engine 132. In some example, the controls 417B may provide a non-static identifier for the CV search engine 132. The second asset 400B may include a sensor, probe, and/or treatment applicator 425B configured to be coupled to the asset body 420B.

For the sake of illustration, the second asset 400B may include an antenna 440 mounted somewhere on the asset body 420B or a monitor device 410B for communication of patient monitoring data to the PMS 145. In an embodiment, the antenna 440 may be removable when the second asset 400B is not in use and may be a distinguishing factor for determining availability of an asset and/or asset class. For example, the presence of antenna 440 or its connector if the antenna is removed may distinguish the asset as being in a class associated with the PMS 145.

By way of non-limiting example, the non-static identifier for the CV search engine 132 may include displays similar to those shown in FIG. 3A. Thus, assuming the second asset 400B is operational, then display fields similar to those shown in FIG. 3A may be viewed on a display screen 415B and extracted for identifying in-use status of the asset.

Figures 4C, 4D:
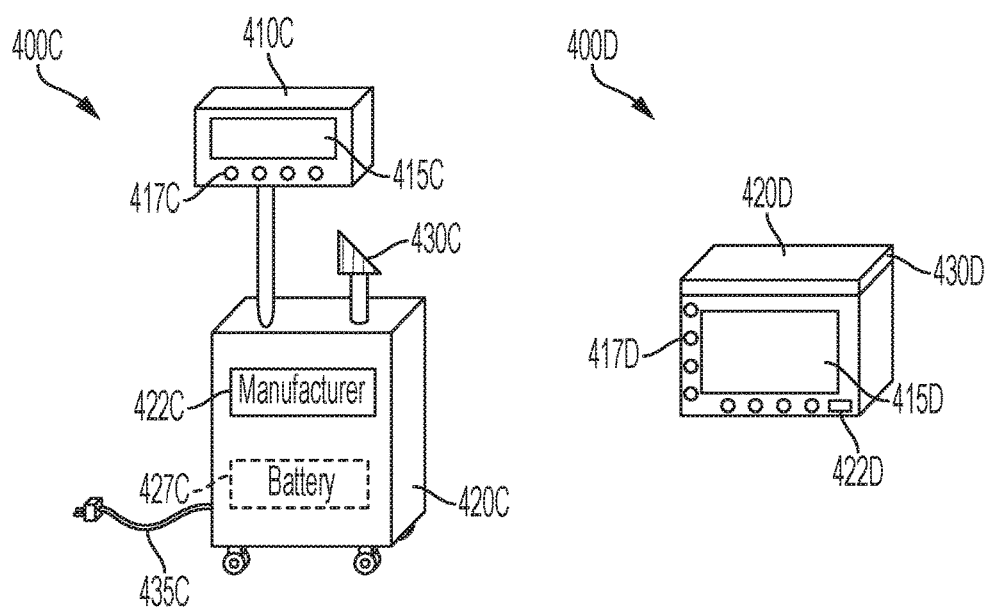
FIG. 4C illustrates an example of a third asset.
FIG. 4D illustrates an example of a fourth asset.

FIG. 4C illustrates an example of a third asset 400C. The third asset 400C may include an asset body 420C. The asset body 420C may include wheels. The asset body 420C does include a power cord 435C but may also include a battery 427C which is not visible externally, as denoted by the dashed box. The third asset 400C may include a first static identifier field 422C and a second static identifier field 430C, the third static identifier field being denoted as vertical line hatching on a flag. The third asset 400C may include a monitor device 410C having a display screen 415C. The third asset 400C may include controls 417C. As can be seen the monitor device 410C may have a different shape or size than monitor devices 410A and 410B. Likewise, the asset body 420C may have a different wheel configuration than the other asset bodies of FIGS. 4A and 4B. By way of non-limiting example, any distinguishing factor between asset bodies can be used for identification and classification purposes. Thus, any of the differences described herein should not be considered limiting list of differences extracted and evaluated in any way.

The display screen 415C may provide a non-static identifier (not shown) for the CV search engine 132. In some example, the controls 417C may provide a non-static identifier for the CV search engine 132. The controls 417C are shown oriented below the display screen 415C. Thus, the configuration of the controls 417A, 417B and 417C may be a distinguishing factor when identifying an asset.

FIG. 4D illustrates an example of a fourth asset 400D. The fourth asset 400D may include an asset body 420D. The asset body 420D may be configured as a monitoring device with a display screen 415D such as a telemetry unit. The asset body 420D may include controls 417D. The asset body 420D does not include wheels and may place the fourth asset 400D in a different asset class for extracting information. The asset 400D may include a power cord (not shown) and/or internal battery (not shown).

The fourth asset 400D may include a first static identifier field 422D which may be on a front of the monitoring device. The fourth asset 400D may include a second static identifier field 430D. The second static identifier field 430D is represented as the band around the asset body 420D which can be visible up to 360 degrees.

The assets described relation to FIGS. 4A-4D are electronic asset devices. However, tracked assets may include, without limitation, wheelchairs to transport patients, intravenous (IV) poles to hang IV solutions, transport beds or vehicles, medicine carts, or other non-electronic assets. Non-electronic assets may include mobile or movable assets. The determination of availability may be based on a determination of whether the asset is occupied, unoccupied, or in transport (i.e., in motion).

In various embodiments, additional and/or alternate assets may be used within the scope of this disclosure. While, the disclosure herein is directed to a hospital setting, the aspects of the embodiments are applicable with environments with mobile assets that need to be tracked to determine real-time availability.

FIG. 5 illustrates an example asset record 500. The asset record 500 may include one or more of the following data: manufacturer information 502, model 504, make 506, dimensions 508, power type 510, color 512, static tag identifier 514, a set of asset image(s) 516, asset identification (ID) 518, and asset name 519. The manufacturer information 502, model 504, make 506, dimensions 508, power type 510, and color 512 include information which may be provided by the manufacturer and used to populate the asset record 500.

The set of asset images(s) 516 may include "ON" state sub-set of images 572, an "OFF" state sub-set of images 574 and asset feature images 576. The asset feature images 576 may be used to identify an asset initially. The "ON" state sub-set of images 572 and "OFF" state sub-set of images 574 will be described in more detail later.

The data for the model 504 may include non-static visual indicator features 532 and accessories 534. Accessories 534 may include a sensor, probe, and/or treatment applicator (i.e., treatment applicator 425A or 425B). The non-static visual indicator features 532 may include a model graphical user interface (GUI) 542, model controls 544 and model power indicators 546. For example, the model GUI 542 may include a display screen similar to display screen 320A. The model controls 544 may include information associated with the layout of controls (i.e., controls 417A, 417B or 417C), whether any control illuminates, and the color of illumination. The power indicators may include a visible display or illumination of a control to represent the asset's machine is in an "ON" state. Features which distinguish an "ON" state may be used for determining current real-time availability of the asset.

The power type 510 may include information associated with an internal battery configuration 552, an external battery configuration 554 and a combination external/internal battery configuration 556. The static tag identifier 514 may include one or more of a tag color 562, a tag type 564 and a tag location 566. A tag type 564 may include a tag ribbon, a tag flag, tag band and a tag strip. In some embodiments, the tag type when installed or applied to the asset, the static tag identifier 514 can be seen up to 360 degrees. In an embodiment, the tag or the second static identifier field is permanently affixed to the asset body. The first static identifier field is generally affixed by the manufacturer. Thus, the first static identifier field may be affixed by the manufacturer without the need to alter the manufacturing processes.

In various embodiments, additional and/or alternate asset record data may be used within the scope of this disclosure.

Figure 6:
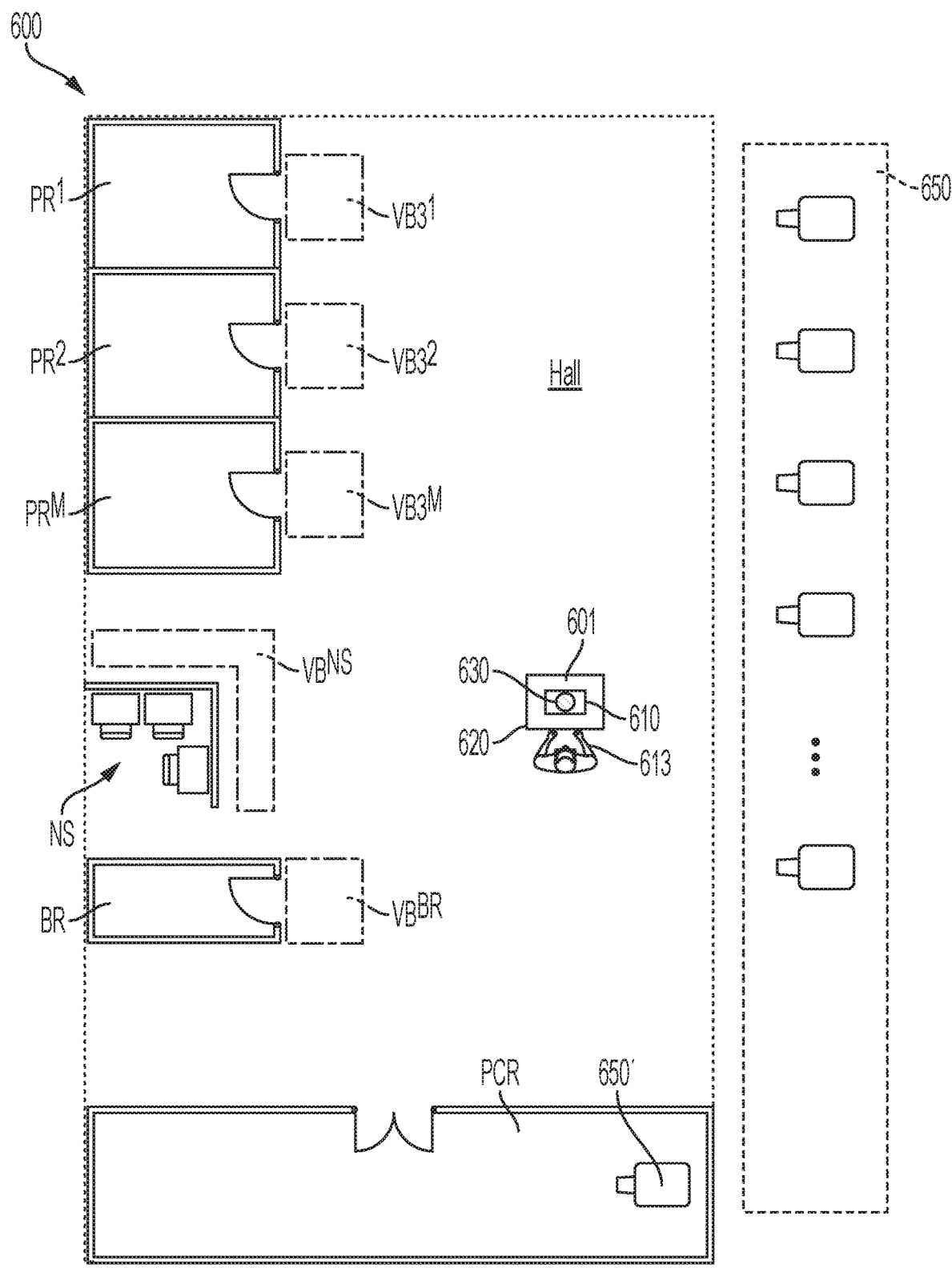
FIG. 6 illustrates an example floor with a plurality of locations.

FIG. 6 illustrates an example floor 600 with a plurality of locations. The tracking and/or locating of an asset 601 may require a search using images from imaging device over one or more floors. The floor 600 has a plurality of patient rooms $PR^1$, $PR^2$, . . . , $PR^M$. The floor 600 may have at least one nursing station NS. The floor 600 may include a plurality of imaging devices 650. The floor 600 may include identifiable landmarks such as doors, plaques, and other distinguishing features associated with a location within the floorplan of the floor 600. For example, doors may identify patient rooms, procedure rooms, public bathrooms, break rooms and supply closets. One or more of the landmarks may be associated with a virtual boundary as will be described in more detail.

For example, a virtual boundary $VB^{NS}$ may be associated with an area by the nursing station NS. The virtual boundary $VB^{BR}$ is an area in proximity to the door of the bathroom BR. In an embodiment, virtual boundaries $VB3^1$, $VB3^2$, . . . , $VB3^M$ may be associated with and in proximity to patient rooms $PR^1$, $PR^2$, . . . , $PR^M$. The reference "M" is a non-zero integer number. In view of the description herein, the placement of a virtual boundary should not be limited to the locations described in relation to FIG. 6. Describing the location of each and every virtual boundary is prohibitive. These virtual boundaries are examples of how such boundaries may be used.

In FIG. 6, assume that an employee 613 is walking along a hall of the floor 600 with an asset 601 wherein portions of the asset body 620, a monitor device 610 and a second static identifier field 630, shown from a top view. The virtual boundaries will be described in the context of the layout of the floor 600 example.

In a case where the employee 613 goes to the bathroom at bathroom BR, the employee 613 may leave the asset 601 in the area of the virtual boundary $VB^{BR}$. The virtual boundary $VB^{BR}$ and/or bathroom BR may be identifiable based on landmarks. For example, adjacent to the bathroom door or on the bathroom door a plaque may indicate the presence of a public bathroom. The plaque or landmark may be captured by one or more imaging devices of the plurality of imaging device 650. In this case, the employee 613 may still have need for the asset 601 although the asset 601 is idle. Hence, the system 100 may use a timing adjustment for re-checking the status of the asset 601 for a predetermined amount of time before finalizing the availability identification. The asset 601 may be located but the availability identification process may be delayed when the asset 601 is in or in close proximity to a designated virtual boundary area.

For example, an employee 613 may stop at the nursing station NS to review the chart of the patient before proceeding with the asset 601 to the patient's room. Assume for the sake of example, the employee 613 places the asset 601 in or in close proximity to the virtual boundary $VB^{NS}$ and proceeds to review the chart prior to proceeding to the patient's room. Each virtual boundary may have its own timing adjustment. Nonetheless, an employee 613 may have placed the asset 601 in the virtual boundary $VB^{NS}$ because they are done with the asset 601. In other words, the asset 601 is available. The asset's availability may be determined if the asset remains in the area associated with the virtual boundary and the timing adjustment expires.

The imaging devices 650 are shown to the right of the floor. The imaging devices 650 may be located throughout the floor including the ceiling and/or walls along the corridor of the hall.

The patient rooms $PR^1$, $PR^2$, . . . , $PR^M$ may, for example, not include an imaging device. Thus, an asset 601 may be detected at a location of a patient room, such as patient room $PR^1$, via the extraction of image data of one or more landmarks representative of or associated with the patient room $PR^1$. For example, if the employee 613 entered and exited the virtual boundary $VB3^1$ through the door of the patient room $PR^1$, the machine learning algorithms 136 (FIG. 1) may classify the asset 601 as being located in patient room $PR^1$. Thus, a timing adjustment may be set for the use of the asset 601 to perform its intended function. However, depending on the type of asset and if the asset does not exit the patient room after the timing adjustment, the asset 601 may be flagged as available with the location marked as the patient room PR[1]. In other embodiments, if the asset 601 is detected existing the patient room PR[1] with the employee, the timing adjustment may be caused to expire.

The floor 600 may include a procedure room PCR. In an embodiment, a procedure room may include one or more imaging devices 650' to capture images or video of a procedure using an asset. The procedure room PCR may be for conducting medical procedures such as surgeries or medical therapy. Although not shown, the procedure room PCR may have a virtual boundary at the door.

In various embodiments, additional and/or alternate virtual boundaries may be used within the scope of this disclosure.

Figure 7A:
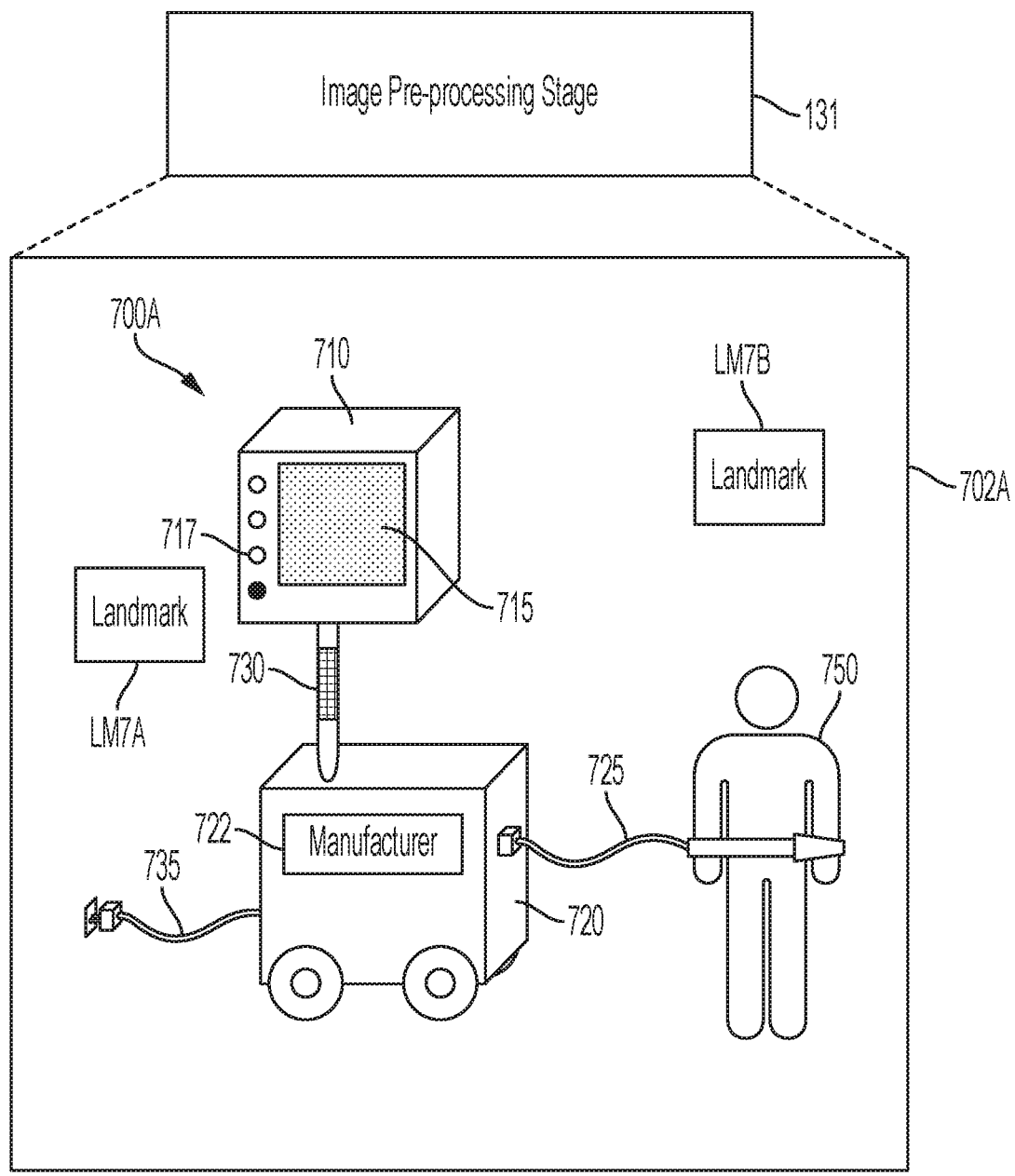
FIG. 7A illustrates an example input image of an unavailable asset at a location.
Figure 7B:
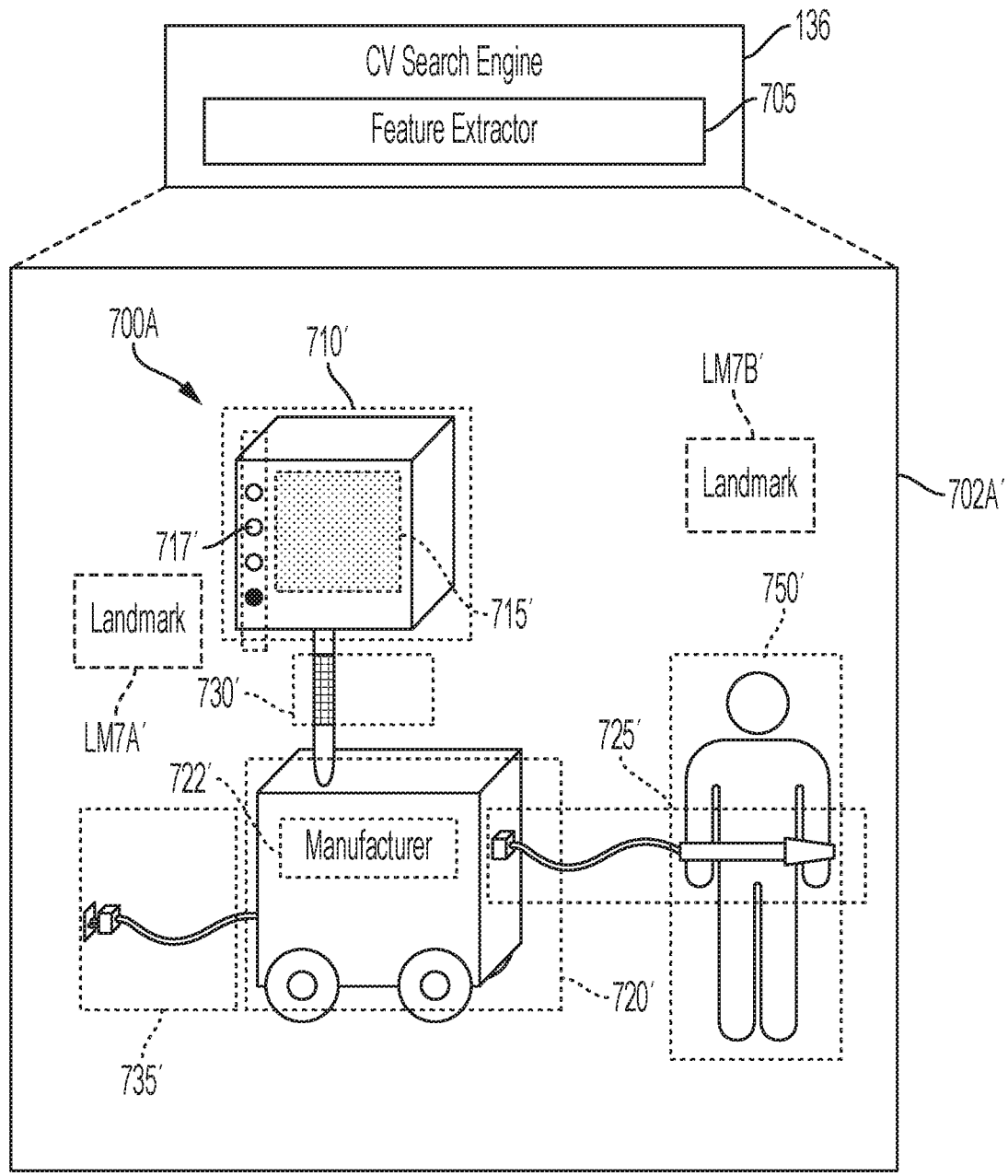
FIG. 7B illustrates an example image of the unavailable asset with asset features and location features being bounded for extraction.
Figure 7C:
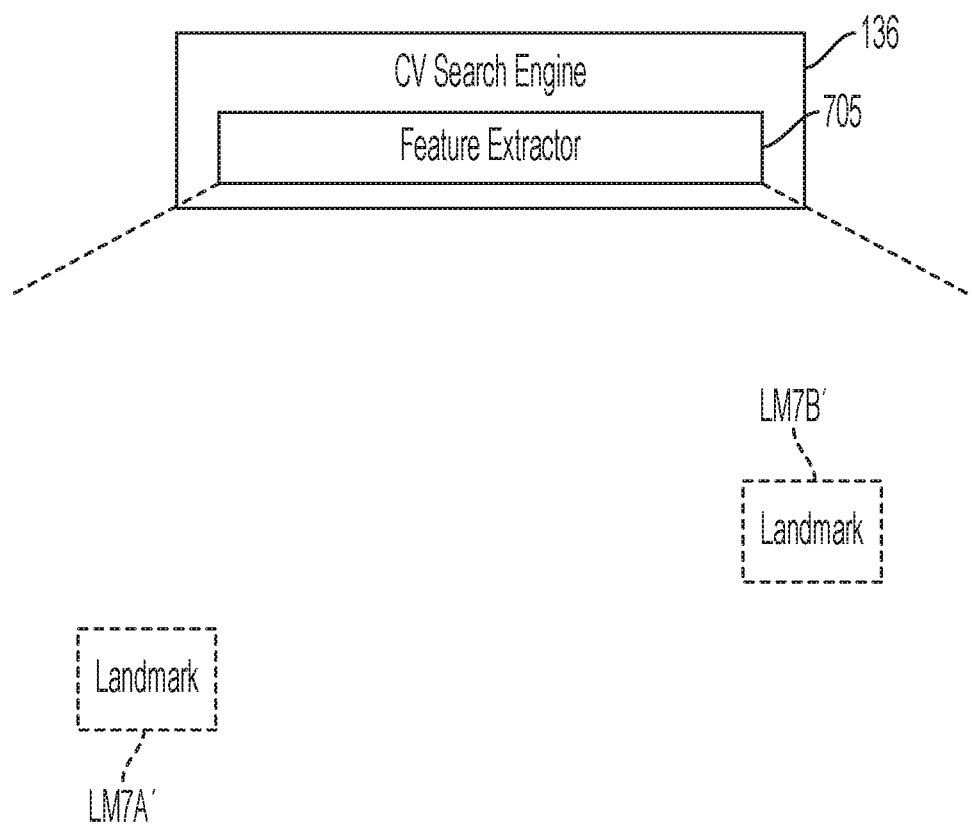
FIG. 7C illustrates example bounded landmark extracted features.
Figure 7D:
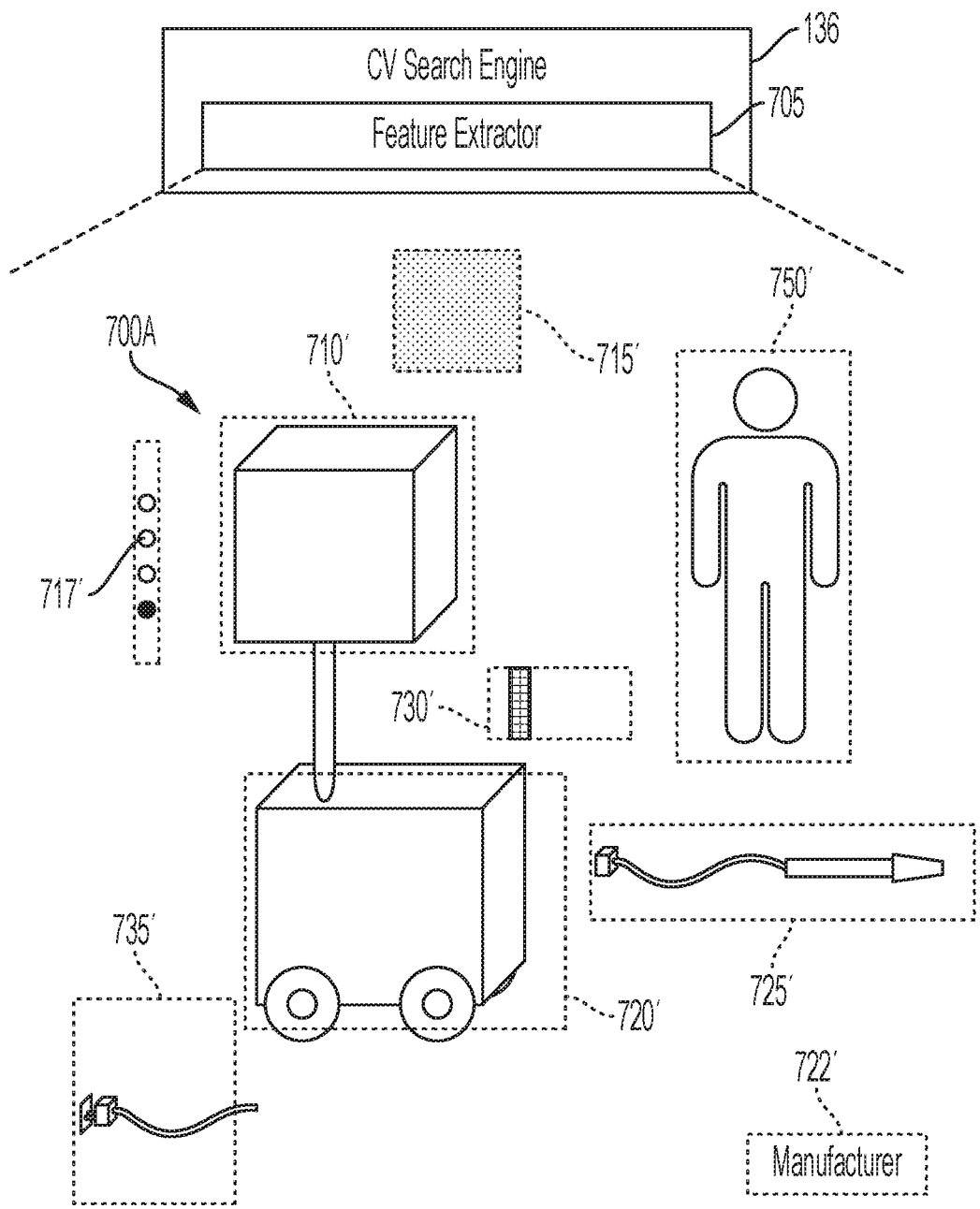
FIG. 7D illustrates example bounded asset extracted features for use by the asset classifier of the machine learning algorithms.

The image pre-processing state 131, the CV search engine 132 and the machine learning algorithms 136 will be described in relation to FIG. 7A-7D. FIG. 7A illustrates an example input image of an unavailable asset at a location. FIG. 7B illustrates an example image of the unavailable asset with asset features and location features being bounded for extraction. FIG. 7C illustrates example bounded landmark extracted features. FIG. 7D illustrates example bounded asset extracted features for use by the asset classifier of the machine learning algorithms.

FIG. 7A illustrates an example input image 702A of an unavailable asset 700A at a location. The asset 700A may include an asset body 720. The real-time video stream from the one or more imaging devices 150 or 650 may be pre-processed and converted to still images to create the input image 702A, for example, by the image pre-processing stage 131. The asset body 720 may include wheels and a power cord 735. In the input image 702A, power cord 735 is plugged into a wall outlet which may be extracted by the feature extractor 705. In some embodiments, the asset body 720 may be distinguishable by one or more of other static identifiers such as a body color, a body shape, a body size, and a body surface texture.

The asset 700A may include a first static identifier field 722 and a second static identifier field 730, the second static identifier field being denoted as square hatching. The asset 700A may include a monitor device 710 having a display screen 715. The asset 700A may include controls 717. In the image 702A, the bottom control of controls 717 is illuminated to indicate that the asset is powered. Furthermore, the screen 715 is shown with dotted hatching to indicate that the monitor device 710 is also operational and displaying information or an illuminated screen. The asset 700A may include a sensor, probe, and/or treatment applicator 725 configured to be coupled to the asset body 720. In some embodiments, the sensor, probe, and/or treatment applicator 725 may be removably attached. In other embodiments, the sensor, probe, and/or treatment applicator 725 may be permanently attached. Nonetheless, a sensor, probe, and/or treatment applicator 725 may be identified and extracted to determine a type of asset, a timing adjustment and/or availability of the asset. In the image 702A, a patient 750 is shown in the input image.

In the image 702A, at least one landmark LM7A and LM7B is shown. The landmarks may be used to identify a current location of the asset 700A, in some embodiments.

The pre-processing stage 131 may detect objects within the still image. From a set of labeled images, as described in FIG. 5, and manufacturer data, labeled features may be identified to identify an object and create predictive model based on the currently captured images. The pre-processing stage 131 may perform image classification. Classification may include acts to predict the presence of an asset of interest (AOI). The AOI may be an asset identified in a query. The pre-processing stage 131 may predict the type or class of an object in an input image. The output of the pre-processing stage 131 may include a class label (e.g. one or more asset labels that are mapped to respective asset). An asset label may be a static indicator.

In some embodiments, one or more of the functions of the pre-processing stage 131 may be performed by the feature extractor 705. The data analytics may be performed by of the CV search engine 132 using known feature extraction techniques, such as without limitation, pixel processing techniques, Haar wavelets, color histograms, edge detection techniques, and text feature extraction techniques. This list is not an exhaustive list of feature extraction techniques. Other feature extraction techniques to extract features and objects from images may be used.

FIG. 7B illustrates an example image 702A' of the unavailable asset with asset features and location features being extracted, by a feature extractor 705 of the CV search engine 132. In FIG. 7B, the example image 702A' is essentially the same as input image 702A but with bounding boxes shown, denoted by the dashed boxes. Extracted features from the still images can be feed to a predictive model, sometimes referred as a machine learning model. The asset features being extracted, by the feature extractor 705, may include one or more of those features denoted in a bounding box.

The feature extractor 705 may use object localization to locate the presence of objects in an input image 702A and indicate their location (pixel references) relative to the image area with a bounding box, represented as the dashed line boxes. The input image 702A is an image with one or more objects, such as an asset picture. The output of the feature extractor 705 may include the one or more bounding boxes (e.g. defined by a point, width, and height) and a class label for each bounding box.

The feature extractor 705 may detect an object and mark the pixel locations of the presence of object with a bounding box within the image area. The marked feature can be extracted from the image for further processing to detect types or classes of the located objects in an image. For example, located objects may include the power cord 735 but also objects such as an output plug.

By way of non-limiting example, the asset 700A may include a bounding box 720' which extracts or marks those pixels of the image representative of the asset body 720. In the image, power cord 735 is plugged into a wall outlet which may be extracted by the feature extractor 705 wherein the bounding box is denoted as 735'. The bounding box 735' extracts or marks those pixels of the image representative of power cord 735 plugged into a wall outlet. The detection by the machine learning algorithm 136 of the power cord plugged into the wall outlet may be an indicator of in-use status of the asset 700A. However, it may not be the only indicator. For example, the asset 700A could be plugged in but turned off.

The bounding box 722' extracts or marks those pixels of the image representative of the first static identifier field 722. A bounding box 730' extracts or marks those pixels of the image representative of the second static identifier field 730. Extraction, by the feature extractor 705, and detection, by the machine learning algorithm 136, of the identifier fields 722 and 730 may identify the asset type, asset identifier and asset name. In some embodiments, if the first static identifier field 722 and the second static identifier field 730 were identified in the pre-processing stage 131, the generation of the bounding box 722' and/or 730' may be omitted.

The bounding box 710' extracts or marks those pixels of the image representative of the monitor device 710 having a display screen 715. Bounding box 715' extracts or marks those pixels of the image representative of the display screen 715. The bounding box 717' extracts or marks those pixels of the image representative of the controls 717. In the image, the bottom control of controls 717 is illuminated to indicate that the asset is operational. Thus, these extracted features may be provided to the machine learning algorithm 136 to build a predictive model and identify the current real-time availability of the asset 700A.

The bounding box 725' extracts or marks those pixels of the image representative of the sensor, probe, and/or treatment applicator 725. The bounding box 750' extracts or marks those pixels of the image representative of an object such as the patient 750 in proximity to the applicator 725 or asset. Other objects in proximity to the application 725 may include a hospital bed, for example.

The bounding boxes LM7A' and LM7B' extracts or marks those pixels of the image representative of the at least one landmark LM7A and LM7B to identify a current location of the asset 700A.

In FIG. 7C, the extracted pixels associated with bounding boxes LM7A' and LM7B' representative of landmarks may be processed to identify a current location of the asset 700A. By way of non-limiting example, the landmark LM7A may be a plaque in a room, wherein the plaque would identify the room in which the asset is located. In other embodiments, the imaging device if in the room may be used as the location identifier. Hence, the location prediction using a location prediction model may be skipped in some instances.

For example, in the emergency room an imaging device may identify its location as the emergency room. However, the at least one landmark LM7A and LM7B may be used to provide more information to the user such as which room in the emergency room the asset is located.

In FIG. 7D, the bounding boxes 710, 715', 717', 720', 722', 725', 730', 735' and 750' are shown separated out from the other. The bounding boxes includes extracted image data is represented as a region or area in the image. The feature of a bounding box is computed. In this context, "computing" may include computing or logging pixel information input to the predictive model. For example, with the bounding box 117', the system may look for one or more control buttons which distinguishes the "ON" state and "OFF" state of the asset. The computing may require determining the size of the controls 117 and search or hunt for a set of pixels representative of the controls 117. Then, a particular button which would be illuminated if the asset is in the "ON" state. Consequently, those pixels that should contain an illuminated control button is searched for to determine an "ON" state.

For example, the computing may require determining the size of a feature and searching for those pixels relative to the bounding box or object in the bounding box that would indicate the "ON" state or "OFF" state of the asset. The computing may include determining a pixel match in color, texture, brightness, or other feature between one or more pixels of the bounding box of the captured real-time image and a stored asset image.

The pixels of the bounding boxes may be compared to the asset's stored images and/or a universal set of images associated with the asset. The image data of the bounding boxes may use by the asset classifier of the machine learning algorithms.

A machine learning model may be developed with images of common set of assets used in hospitals worldwide and will continuously identify the assets that are in hospital.

Manufacturer Data:

For the hospital assets which need asset tracking and availability report(s), details like manufacturer name, model number, dimensions and aesthetics (color, texture) of the devices may be fed once into the machine learning model. Feeding the data can be done through a software application that resides on a computer. If the computer is connected to the internet, the user can also load the details to the model by simply searching the device make and model, for example, from a setup asset application available in a computer of the system 100. The set-up asset application automatically queries the required information and feeds to the machine learning model.

Labeled Assets Image Data:

A set of images of assets labeled or tagged may be fed to the Machine Learning Model as inputs. For example, if the asset is a medical ventilator machine, images of various models of ventilators can be labeled or tagged and fed into the algorithm. Images may be labeled to identify the operating condition of the device, as well. In case the ventilator is in an "OFF" condition, the display screen of the ventilator machine may be in an "OFF" condition. Another, feature of the image may be that the ventilator machine is not connected to a patient.

For example, the set of images may identify different classifications or sub-classification of the asset. The set of images may include one or more images that identify an "ON" state of the asset or "OFF" state of the asset. The set of images may include one or more images of the controls or the display screen to distinguish the "ON" state of the asset or "OFF" state of the asset. Describing each and every image may be prohibitive. The set of images may include a first sub-set of images for an "ON" state of the asset. The set of image may include a second sub-set of images for an "OFF" state of the asset.

In an embodiment, the first sub-set of images for identifying an "ON" state of the asset may include images of the sensor, probe, and/or treatment applicator 725 attached to a patient. By way of non-limiting example, assume the asset is a ventilator machine. The images may capture a ventilator tubing attached to a patient as part of the "ON" state determination.

One or more features of the first sub-set of images may be weighted higher in the machine learning algorithm than other features. For example, certain features for images in the "ON" state sub-set of images 572 when used in the determination of the "ON" state may have a higher weight indicative of in use or unavailable. Assume an asset such as a ventilator machine. The system 100 may place a higher weight for extracted features, such as the presence of the ventilator tubing attached to a patient in the current image for use in the machine learning algorithm. The asset could be detected or predicted as in an "ON" state (unavailable) with the display device on and power cord connected to a wall outlet. However, without the ventilator tubing connected to the patient, the asset could be running idle. Thus, the predictive model may impose a timing adjustment to the availability prediction phase to see if the state of the asset changes. Likewise, one or more extracted features associated with the "OFF" state sub-set of images 574 may be weighted higher in the machine learning algorithm to indicate an "OFF" state (available). For example, if the asset requires only an external power and the power cord is not connected to a power outlet, then such feature extraction may be weighted higher in the machine learning algorithm.

In various embodiments, additional and/or alternate image data may be used within the scope of this disclosure to determine availability and a location of the asset.

The quality of patient care depends on the uninterrupted availability and sustained interaction of a multitude of technological and medical devices. When the staff can perform their duties without any trouble caused by lost or misplaced equipment, patients and employees both get to experience streamlined hospital workflows, improving quality healthcare.

Figure 8:
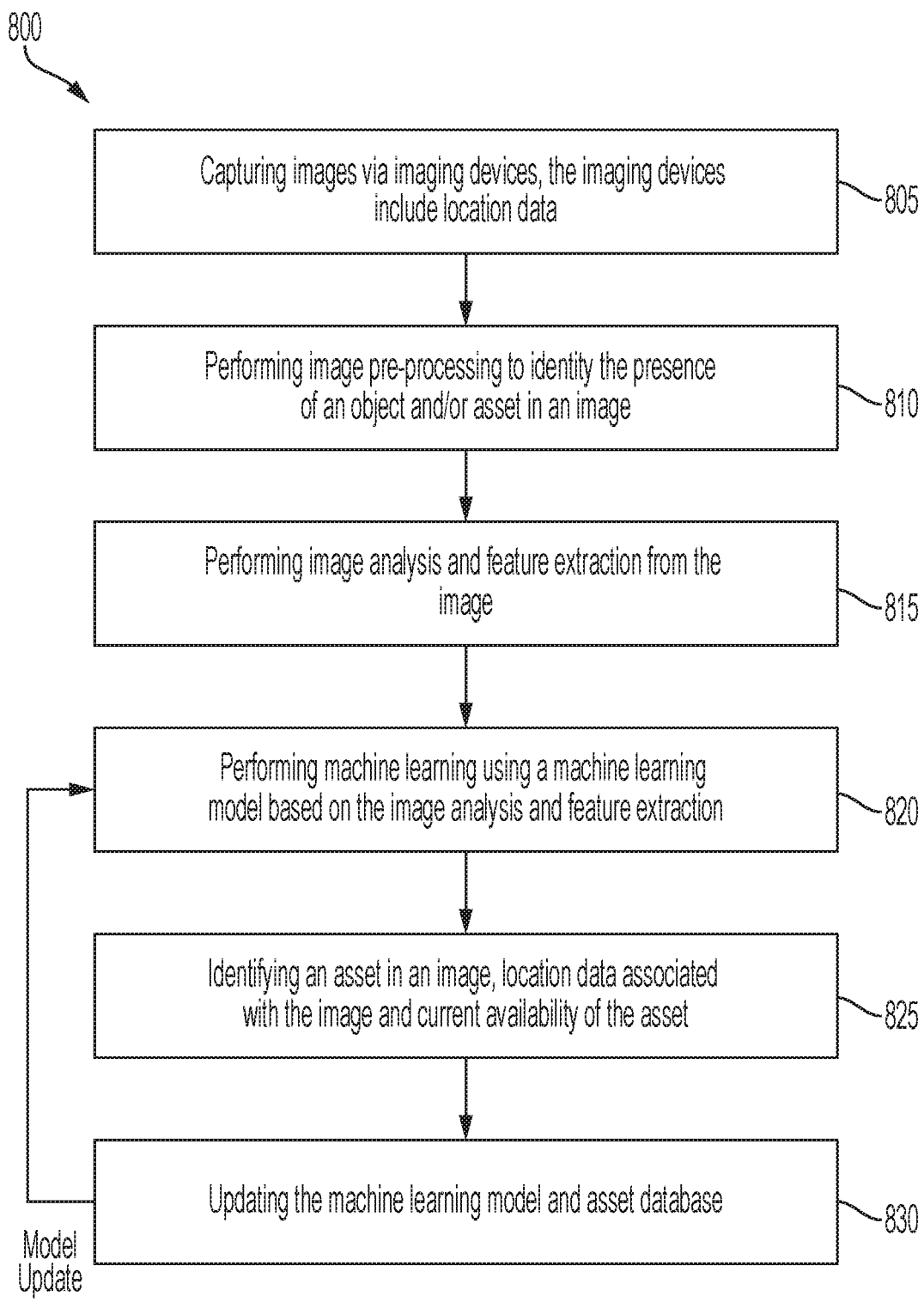
FIG. 8 illustrates an example flowchart of the method for identifying an asset, location data and availability.

FIG. 8 illustrates an example flowchart of the method 800 for identifying an asset, location data and availability. The method is shown with ordered blocks. The blocks may be performed in the order shown or a different order. The one or more of the blocks may be performed contemporaneously. Blocks may be added or omitted.

The method 800 may include, at block 805, capturing images via imaging devices (i.e., imaging device 150 or 650). The imaging device may have location identifiers. In some instances, the location identifiers associated with an imaging device is sufficient to determine a location of an asset. However, in other instances landmark data is desired to determine a location or refine the location data. The method 800 may include, at block 810, performing video pre-processing to obtain images from the video stream. In some embodiments, the pre-processing may obtain objects in the images, such as identify the presence of an asset and/or object in an image.

The method 800 may include, at block 815, performing image analysis and feature extraction from the image. The operations described above in relation to FIGS. 7B-7D may be included in block 815. The method 800 may include, at block 820, performing machine learning using a machine learning model based on the image analysis and feature extraction. The method 800 may include, at block 825, identifying an asset in an image, location data associated with the image and availability. The location data may be based on location identifiers form the imaging device directly and/or landmarks identified in the image.

The method 800 may include, at block 830, updating the machine learning model and asset database. Block 830 may loop back to block 820 so that the model is updated. The asset database may include current inventory tracking information for one, more or all assets with the current availability status of the asset. In an embodiment, the asset's last known location may be stored in the asset database. A user initiated query may cause the system 100 to locate the asset starting with the last known location. If the asset is not at the last known location in the asset database a full search for the asset may be initiated. A full search of the asset may include, starting a search using the imaging devices associated with the floor associated with the last known location. If the asset is not located, then video from imaging devices in an adjacent floor could be used to find the asset. Nevertheless, a full search may hunt for the asset in a predictive manner by processing video streams captured from imaging devices determined to have a higher probability indicator of being in a path of the asset's movement.

Figure 9:
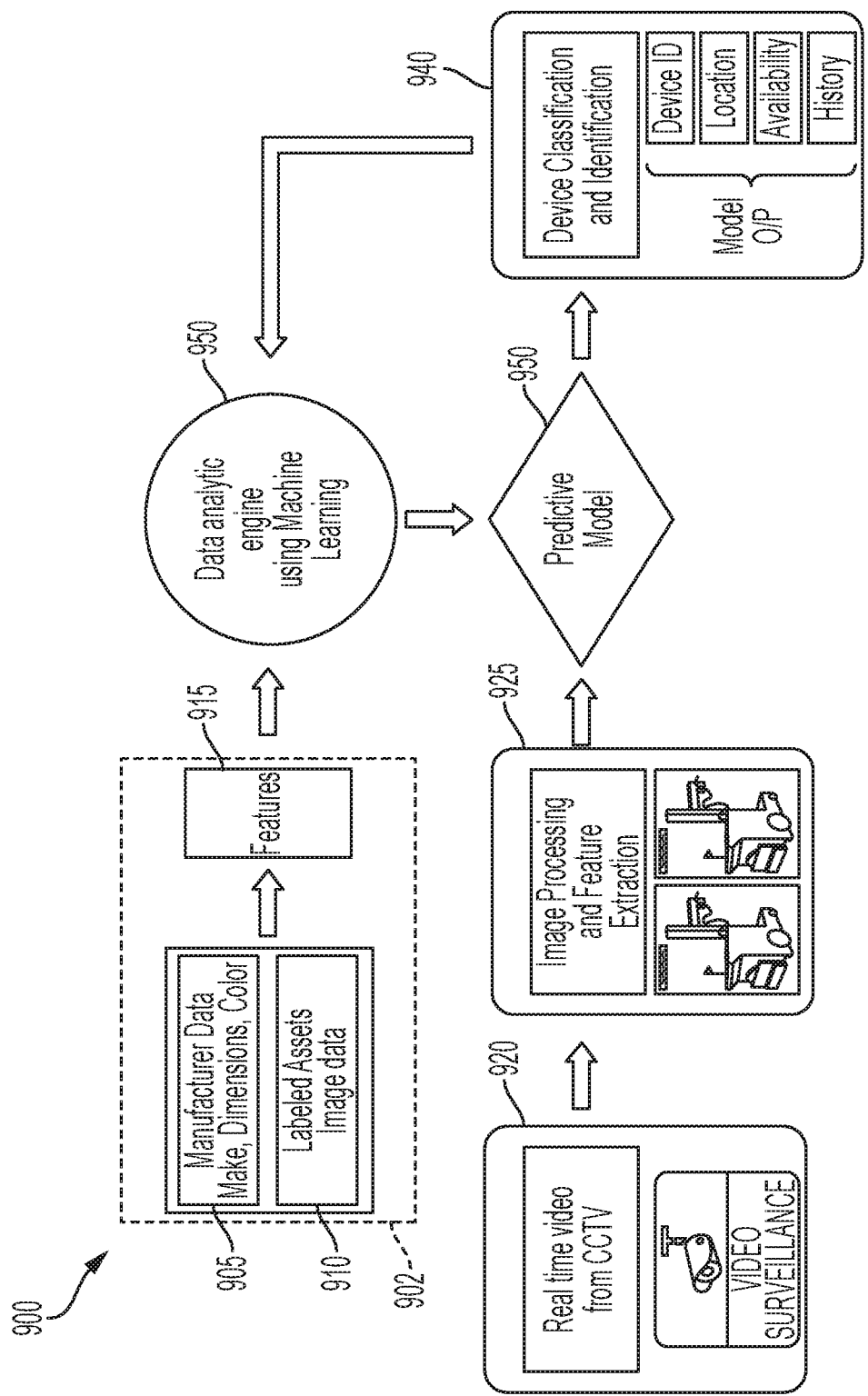
FIG. 9 illustrates an example flow diagram of the system to identify an asset, location data and availability.

FIG. 9 illustrates an example flow diagram 900 of the system 100 to identify an asset, location data and availability. The system 100 may include an asset registration phase at block 902. The asset registration phase may label asset image data, at block 905. The system 100 may upload or enter manufacturing data associated with a new asset, at block 910. The system 100 may include generating a feature set for the asset at block 915. The feature set is sent to a data analytics engine which may interface with machine learning algorithms, at block 940, wherein the data analytics is input into the machine learning algorithms.

During operation the system 100 may capture images, such as video, of the environment, at block 920. In the environment, an asset and/or object may be located. At block 925, the system 100 may perform pre-processing to generate still images of the video stream and perform feature extraction as described above in relation to FIGS. 7A-7D. The image data associated with the boundary boxes generated in FIGS. 7B-7D may be used to generate a predictive model, at block 950. Once a predictive model is complete, the results of the predictive model is sent to the device (asset) classification and identification stage, at block 960. The predictive model will output information that may be classified to identify an asset identifier (ID), location information, availability information and history. The history may identify the length of time the asset has been operational and prior locations. The blocks 940, 950, and 960 may be part of the machine learning algorithms and operations.

The system 100 may be used to locate expensive assets and devices. The system 100 may be used to determine device/equipment idle time and a maintenance/repair schedule.

Figure 10:
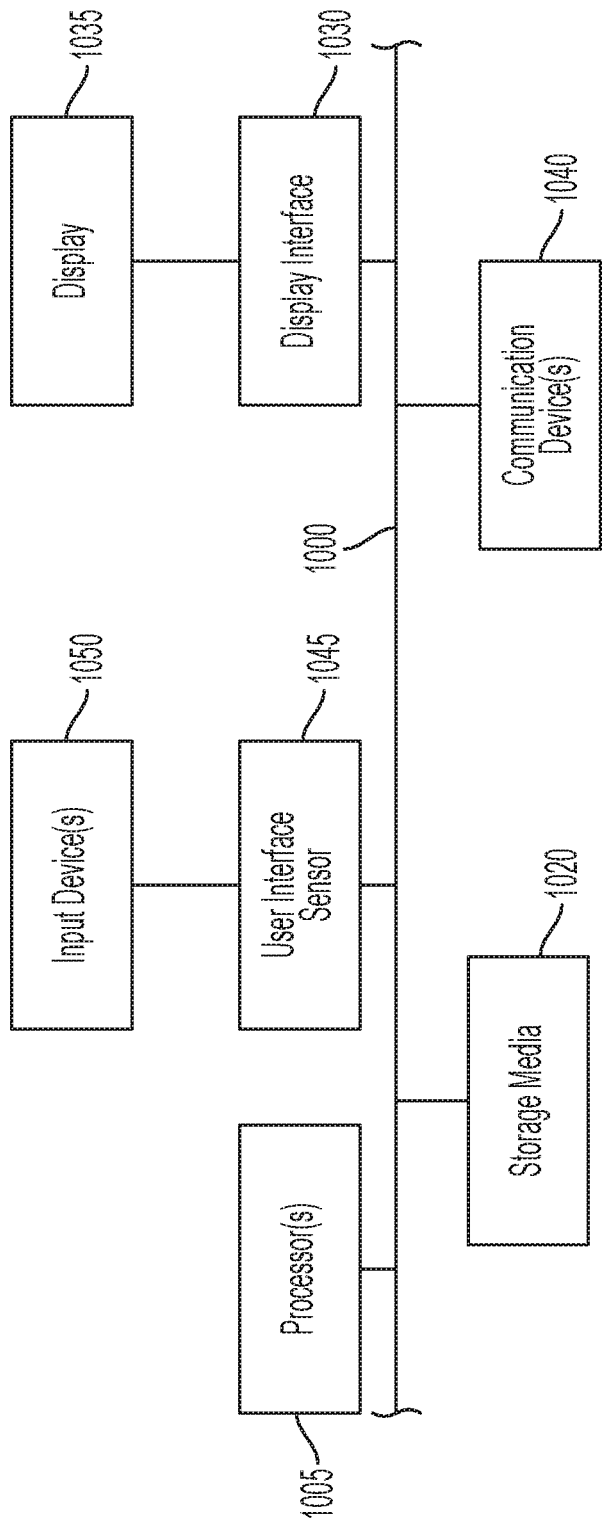
FIG. 10 depicts an example of internal hardware that may be included in any of the electronic components of an electronic device.
Figure 11:
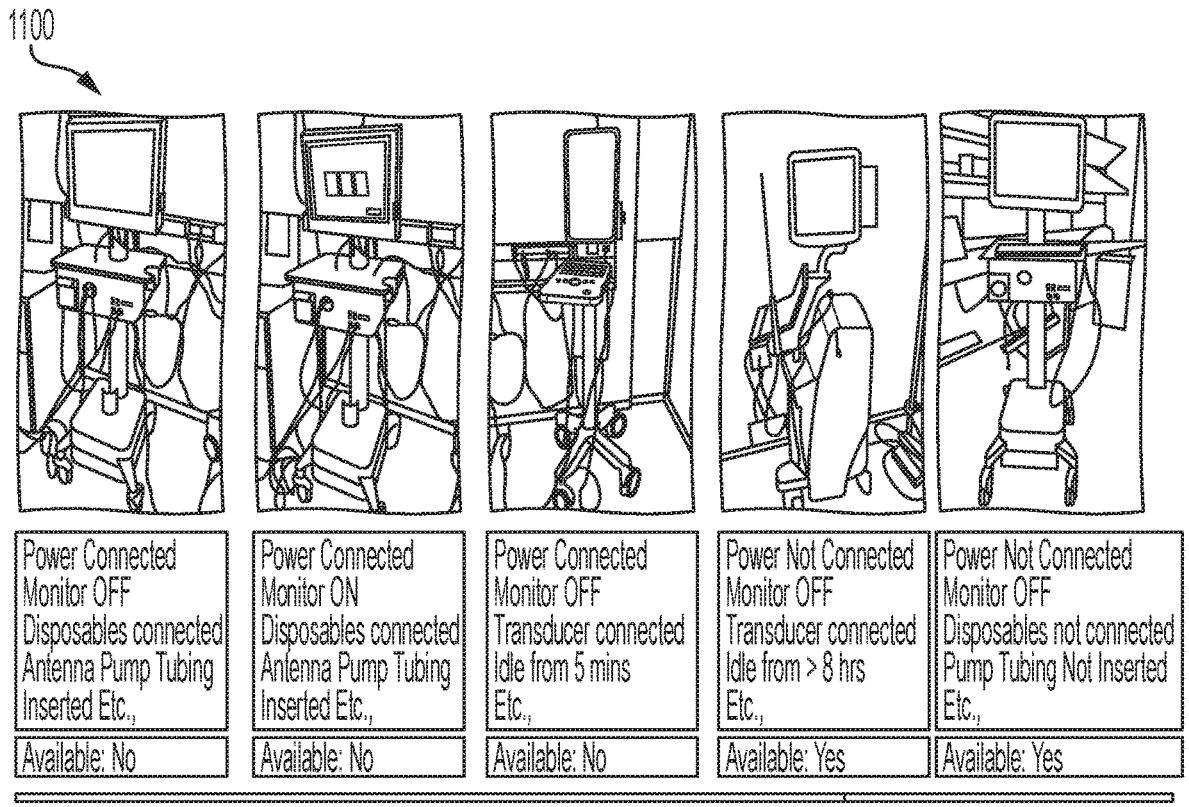
FIGS. 11-14 illustrates different arrangements of tracking results for display by a graphical user interface presenting information associated with assets or subset of assets associated with a fleet.
Figure 12:
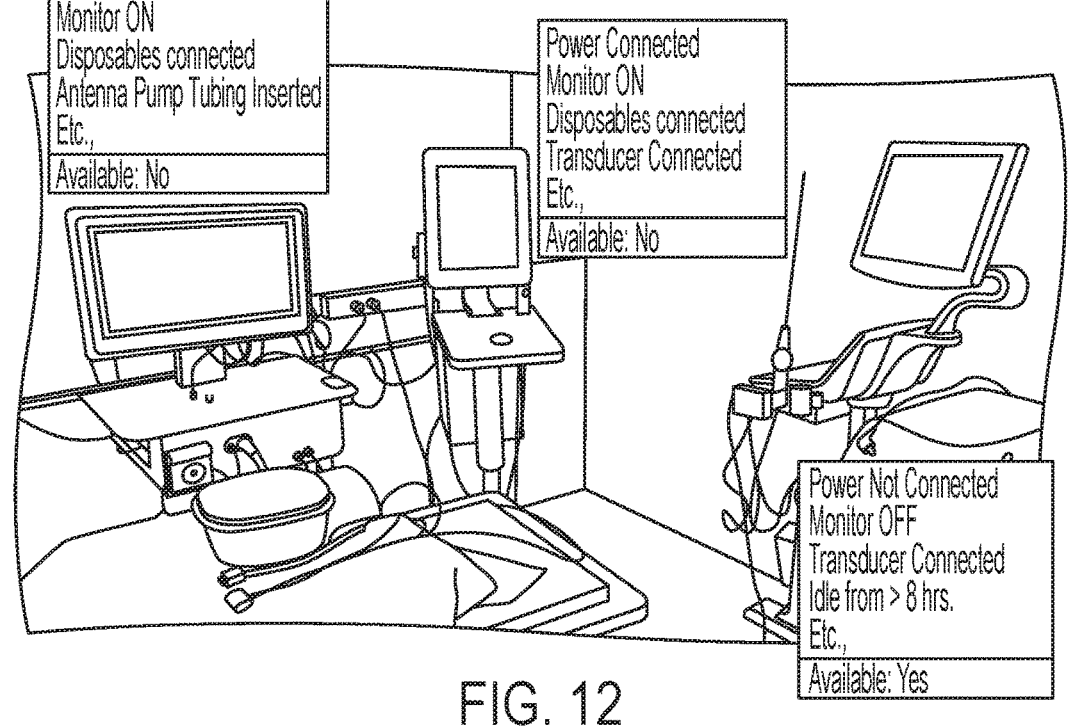
Figure 13:
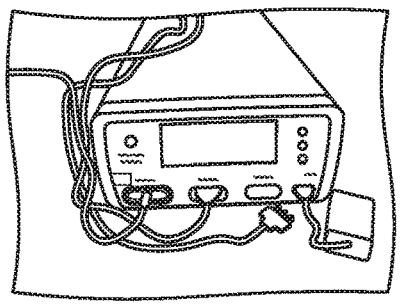
Figure 13:
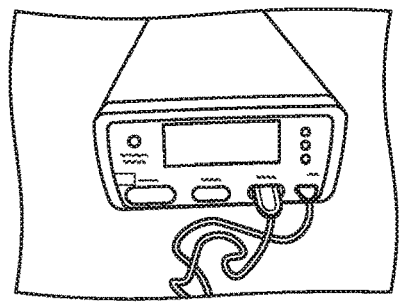
Figure 14:
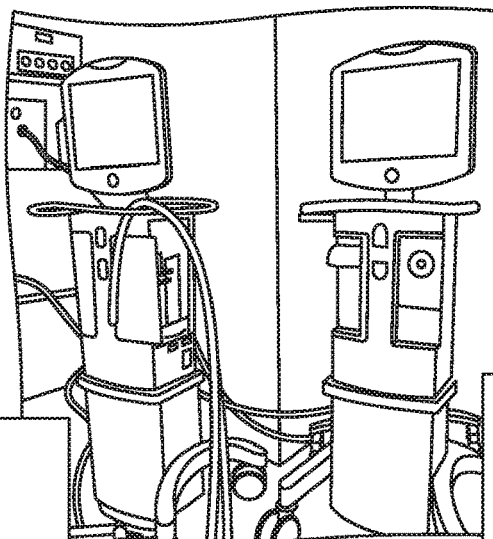

FIG. 10 depicts an example of internal hardware that may be included in any of the electronic components of an electronic device as described in this disclosure such as, for example, an on-premises electronic device, an associate electronic device, a remote electronic device and/or any other integrated system and/or hardware that may be used to contain or implement program instructions.

A bus 1000 serves as the main information highway interconnecting the other illustrated components of the hardware. CPU 1005 is the central processing unit of the system, performing calculations and logic operations required to execute a program. CPU 1005, alone or in conjunction with one or more of the other elements disclosed in FIG. 10, is an example of a processor as such term is used within this disclosure. Read only memory (ROM) and random access memory (RAM) constitute examples of tangible and non-transitory computer-readable storage media 1020, memory devices or data stores as such terms are used within this disclosure. The memory device may store an operating system (OS) of the server or for the platform of the electronic device.

Program instructions, software or interactive modules for providing the interface and performing any querying or analysis associated with one or more data sets may be stored in the computer-readable storage media 1020. Optionally, the program instructions may be stored on a tangible, non-transitory computer-readable medium such as a compact disk, a digital disk, flash memory, a memory card, a universal serial bus (USB) drive, an optical disc storage medium and/or other recording medium.

An optional display interface 1030 may permit information from the bus 1000 to be displayed on the display 1035 in audio, visual, graphic or alphanumeric format. Communication with external devices may occur using various communication ports 1040. A communication port 1040 may be attached to a communications network, such as the Internet or an intranet. In various embodiments, communication with external devices may occur via one or more short range communication protocols. The communication port 1040 may include communication devices for wired or wireless communications.

The hardware may also include an interface 1045, such as graphical user interface (GUI), which allows for receipt of data from input devices such as a keyboard or other input device 1050 such as a mouse, a joystick, a touch screen, a remote control, a pointing device, a video input device and/or an audio input device. The GUIs may be displayed using a browser application being executed by an electronic device and served by a server of the system 100. For example, hypertext markup language (HTML) may be used for designing the GUI with HTML tags to the images of the assets and other information stored in or served from memory 130.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge from which a computer can read. The term non-transitory computer-readable storage medium is used herein to refer to any medium that participates in providing information to processor, except for carrier waves and other signals.

Computer program code for carrying out operations described above may be written in a variety of programming languages, including but not limited to a high-level programming language, such as without limitation, C or C++, Python, and Java for development convenience. In addition, computer program code for carrying out operations of embodiments described herein may also be written in other programming languages, such as, but not limited to, interpreted languages. The program code may include hardware description language (HDL) or very high speed integrated circuit (VHSIC) hardware description language, such as for firmware programming. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed Digital Signal Processor (DSP) or microcontroller. A code in which a program of the embodiments is described can be included as a firmware in a RAM, a ROM and a flash memory. Otherwise, the code can be stored in a non-transitory, tangible computer-readable storage medium such as a magnetic tape, a flexible disc, a hard disc, a compact disc, a photo-magnetic disc, a digital versatile disc (DVD) or the like.

FIGS. 11-14 illustrates different arrangements 1100, 1200, 1300 and 1400 of tracking results for display by a graphical user interface (GUI) presenting information, such as availability and other asset status information, associated with assets or subset of assets associated with a fleet. Other asset status information may include information indicative of whether the power is on, a monitor is on and/or a length of time the asset has been in the present availability status.

In this document, "electronic communication" refers to the transmission of data via one or more signals between two or more electronic devices, whether through a wired or wireless network, and whether directly or indirectly via one or more intermediary devices. Devices are "communicatively connected" if the devices are able to send and/or receive data via electronic communication.

The features and functions described above, as well as alternatives, may be combined into many other different systems or applications. Various alternatives, modifications, variations or improvements may be made by those skilled in the art, each of which is also intended to be encompassed by the disclosed embodiments.

What is claimed is:

1. A system comprising:
a plurality of imaging devices, each imaging device being associated with a known location;
memory having programming instructions stored thereon; and
one or more processors having programming instructions which when executed to cause the one or more processors to:
receive images from at least one imaging device;
detect an object in one or more images;
construct a bounding box around the detected object;
apply a trained machine-learning model to the portion of the images within the bounding box, the machine-learning model trained to identify an asset type based on a set of images associated with the asset type;
identify, by the trained machine-learning model, the asset type of
at least one portable machine in the portion of the images within the bounding box;
predict an operational condition of the portable machine based on the identified asset type, the portion of the images within the bounding box, and a set of images associated with one or more operational conditions of the asset type;
determine a location of the portable machine based in part on the location of the at least one imaging device; and
predict current availability of the at least one portable machine based on the predicted operational condition and determined location.

2. The system of claim 1, wherein the programming instructions to predict availability of the portable machine includes programming instructions which when executed to cause the one or more processors to:
identify a virtual boundary associated with a location;
track an amount of time the portable machine is in the virtual boundary;
determine whether the amount of time exceeds a monitoring threshold of time; and
in response to determining the amount of time exceeds the monitoring threshold of time, identify the portable machine as available.

3. The system of claim 2, wherein the programming instructions to identify a virtual boundary associated with the location includes programming instructions which when executed to cause the one or more processors to:
identify location landmarks in proximity to the portable machine;
identify a virtual boundary type based on the identified location landmarks; and
select the monitoring threshold for the identified virtual boundary type.

4. The system of claim 1, wherein the programming instructions to identify the asset type of the at least one portable machine includes programming instructions which when executed cause the one or more processors to:
search for and recognize, in the one or more images, at least one of:
static visual indicator feature of the portable machine;
at least one non-static visual indicator feature of the portable machine;
power supply equipment;

screen of a display device associated with the portable machine;
a disposable accessory tool coupled to the portable machine;
probe configured coupled to the portable machine; and
accessory of the portable machine.

5. The system of claim 1, wherein the programming instructions to predict availability of the portable machine includes programming instructions which when executed to cause the one or more processors to:
predict a state of availability wherein the state of availability includes one of currently available, imminently available, imminently unavailable and in use; and
generate a display on a graphical user interface (GUI), the display including an image representative of the at least one portable machine, the location of the at least one portable machine and the predicted state of availability, in response to a query for the at least one portable machine entered using the GUI.

6. The system of claim 1, wherein the programming instructions to predict availability of the portable machine includes programming instructions which when executed to cause the one or more processors to:
recognize a wireless transmission unit coupled to the portable machine, the wireless transmission unit being associated with a real-time patient monitoring system; and
in response to recognizing the wireless transmission unit, query the real-time patient monitoring system for operational data associated with the portable machine.

7. A computer-implemented method comprising:
by one or more processors:
receiving images from at least one imaging device having a known location;
detecting an object in one or more images;
constructing a bounding box around the detected object;
applying a trained machine-learning model to the portion of the images within the bounding box, the machine-learning model trained to identify an asset type based on a set of images associated with the asset type;
identifying, by the trained machine-learning model, the asset type of
at least one portable machine in the portion of the images within the bounding box;
predicting an operational condition of the portable machine based on the identified asset type, the portion of the images within the bounding box, and a set of images associated with one or more operational conditions of the asset type;
determining a location of the portable machine based in part on the known location of the at least one imaging device; and
predicting availability of the at least one portable machine based on the predicted operational condition and determined location.

8. The method of claim 7, wherein the predicting availability of the portable machine includes identifying a virtual boundary associated with a location;
tracking an amount of time the portable machine is in the virtual boundary;
determining whether the amount of time exceeds a monitoring threshold of time; and
in response to determining the amount of time exceeds the monitoring threshold of time, identifying the portable machine as available.

9. The method of claim 8, wherein the identifying the virtual boundary associated with the location includes:
Identifying location landmarks in proximity to the portable machine;
identifying a virtual boundary type based on the identified location landmarks; and
selecting the monitoring threshold for the identified virtual boundary type.

10. The method of claim 7, wherein identifying the asset type of the at least one portable machine includes:
searching for and recognizing, in the one or more images, at least one of:
static visual indicator feature of the portable machine;
at least one non-static visual indicator feature of the portable machine;
power supply equipment;
screen of a display device associated with the portable machine;
a disposable accessory tool coupled to the portable machine;
probe configured coupled to the portable machine; and
accessory of the portable machine.

11. The method of claim 7, wherein the predicting availability of the portable machine includes:
predicting a state of availability wherein the state of availability includes one of currently available, imminently available, imminently unavailable and in use; and
generating a display on a graphical user interface (GUI), the display including an image representative of the at least one portable machine, the location of the at least one portable machine and the predicted state of availability, in response to a query for the at least one portable machine entered using the GUI.

12. The method of claim 7, wherein the predicting availability of the portable machine includes:
recognizing a wireless transmission unit coupled to the portable machine, the wireless transmission unit being associated with a real-time patient monitoring system; and
in response to recognizing the wireless transmission unit, querying the real-time patient monitoring system for operational data associated with the portable machine.

13. A tangible and non-transitory computer readable medium having programming instructions stored thereon which when executed to cause one or more processors to:
receive images from at least one imaging device from a known location;
detect an object in one or more images;
construct a bounding box around the detected object;
apply a trained machine-learning model to the portion of the images within the bounding box, the machine-learning model trained to identify an asset type based on a set of images associated with the asset type;
identify, by the trained machine-learning model, the asset type of
at least one portable machine in the portion of the images within the bounding box;
predict an operational condition of the portable machine based on the identified asset type, the portion of the images within the bounding box, and a set of images associated with one or more operational conditions of the asset type;
determine a location of the portable machine based in part on the known location of the at least one imaging device; and predict availability of the at least one portable machine based on the predicted operational condition and determined location.

14. The computer readable medium of claim 13, wherein the programming instructions to predict availability of the portable machine includes programming instructions which when executed to cause the one or more processors to:
identify a virtual boundary associated with a location;
track an amount of time the portable machine is in the virtual boundary;
determine whether the amount of time exceeds a monitoring threshold of time; and
in response to determining the amount of time exceeds the monitoring threshold of time, identify the portable machine as available.

15. The computer readable medium of claim 14, wherein the programming instructions to identify a virtual boundary associated with the location includes programming instructions which when executed to cause the one or more processors to:
identify location landmarks in proximity to the portable machine;
identify a virtual boundary type based on the identified location landmarks; and
select the monitoring threshold for the identified virtual boundary type.

16. The computer readable medium of claim 13, wherein the programming instructions to identify the asset type of the at least one portable machine includes programming instructions which when executed cause the one or more processors to:
search for and recognize, in the one or more images, at least one of:
static visual indicator feature of the portable machine;
at least one non-static visual indicator feature of the portable machine;
power supply equipment;
screen of a display device associated with the portable machine;
a disposable accessory tool coupled to the portable machine;
probe configured coupled to the portable machine; and
accessory of the portable machine.

17. The computer readable medium of claim 13, wherein the programming instructions to predict availability of the portable machine includes programming instructions which when executed to cause the one or more processors to:
predict a state of availability wherein the state of availability includes one of currently available, imminently available, imminently unavailable and in use; and
generate a display on a graphical user interface (GUI), the display including an image representative of the at least one portable machine, the location of the at least one portable machine and the predicted state of availability, in response to a query for the at least one portable machine.

18. The computer readable medium of claim 13, wherein the programming instructions to predict availability of the portable machine includes programming instructions which when executed to cause the one or more processors to:
recognize a wireless transmission unit coupled to the portable machine, the wireless transmission unit being associated with a real-time patient monitoring system; and
in response to recognizing the wireless transmission unit, query the real-time patient monitoring system for operational data associated with the portable machine.

19. The system of claim 1, wherein the programming instructions to predict the operational condition of the portable machine comprise programming instructions to apply an additional trained machine-learning model to the portion of the images within the bounding box, the additional machine-learning model trained to predict the operational condition of the asset type based on the set of images associated with the one or more operational conditions of the asset type.

20. The method of claim 7, wherein predicting the operational condition of the portable machine comprises applying an additional trained machine-learning model to the portion of the images within the bounding box, the additional machine-learning model trained to predict the operational condition of the asset type based on the set of images associated with the one or more operational conditions of the asset type.

* * * * *